United States Patent
Chen et al.

(10) Patent No.: US 11,912,685 B2
(45) Date of Patent: Feb. 27, 2024

(54) BIPHENYL DIARYL PYRIMIDINE DERIVATIVE WITH AROMATIC HETEROCYCLIC STRUCTURE

(71) Applicant: Fudan University, Shanghai (CN)

(72) Inventors: Fener Chen, Shanghai (CN); Chunlin Zhuang, Shanghai (CN); Li Ding, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/468,447

(22) Filed: Sep. 7, 2021

(65) Prior Publication Data
US 2021/0403449 A1    Dec. 30, 2021

(30) Foreign Application Priority Data
Mar. 8, 2021    (CN) .................. 202110248350.X

(51) Int. Cl.
| | |
|---|---|
| *C07D 401/12* | (2006.01) |
| *C07D 239/48* | (2006.01) |
| *C07D 401/14* | (2006.01) |
| *C07D 403/12* | (2006.01) |
| *C07D 405/12* | (2006.01) |
| *C07D 409/12* | (2006.01) |
| *A61P 31/18* | (2006.01) |

(52) U.S. Cl.
CPC ............ *C07D 401/12* (2013.01); *A61P 31/18* (2018.01); *C07D 239/48* (2013.01); *C07D 401/14* (2013.01); *C07D 403/12* (2013.01); *C07D 405/12* (2013.01); *C07D 409/12* (2013.01)

(58) Field of Classification Search
CPC .. C07D 401/12; C07D 401/14; C07D 239/48; C07D 403/12; C07D 405/12; C07D 409/12
See application file for complete search history.

(56) References Cited

FOREIGN PATENT DOCUMENTS

| | | |
|---|---|---|
| CN | 109053591 A | 12/2018 |
| CN | 111303046 A | 6/2020 |

OTHER PUBLICATIONS

Ding et al. J. Med. Chem. 2021, 64, 10297-10311, publication date (web): Jul. 1, 2021.*

\* cited by examiner

*Primary Examiner* — Rebecca L Anderson

(57) ABSTRACT

This application provides a biphenyl diaryl pyrimidine derivative with an aromatic heterocyclic structure, a pharmaceutically-acceptable salt, a stereoisomer, a hydrate and a solvate thereof, where the biphenyl diaryl pyrimidine derivative is shown in formula (I). This application also provides a pharmaceutical composition containing the biphenyl diaryl pyrimidine derivative, or a pharmaceutically-acceptable salt, a stereoisomer, a hydrate and a solvate thereof, and a pharmaceutically-acceptable carrier. This application further provides a method of treating AIDS by administering a therapeutically effective amount of the pharmaceutical composition to a patient in need.

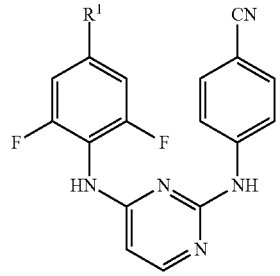

7 Claims, No Drawings

BIPHENYL DIARYL PYRIMIDINE DERIVATIVE WITH AROMATIC HETEROCYCLIC STRUCTURE

CROSS-REFERENCE TO RELATED APPLICATIONS

This application claims the benefit of priority from Chinese Patent Application No. 202110248350.X, filed on Mar. 8, 2021. The content of the aforementioned application, including any intervening amendments thereto, is incorporated herein by reference in its entirety.

TECHNICAL FIELD

This application relates to medicines, and more particularly to a biphenyl diaryl pyrimidine derivative with an aromatic heterocyclic structure.

BACKGROUND

Acquired immunodeficiency syndrome (AIDS) is a major epidemic infectious disease which involves a series of pathogenic infections and tumors caused by human immunodeficiency virus (HIV-1) infection. Since the first case was confirmed by the U.S. Centers for Disease Control (CDC) in 1981, the AIDS has spread rapidly around the world and has become an important global public health problem, and so far, there have been more than 32 million cases died from AIDS.

Reverse transcriptase (RT) plays a key role in the HIV replication cycle, which participates in the reverse transcription of viral RNA into a DNA-RNA hybrid and the degradation of RNA of the hybrid into a single-stranded viral DNA. The single-stranded viral DNA is then integrated into the DNA of host cells under the catalysis of an integrase. Therefore, the RT has become an important target for the design of anti-HIV drugs. Currently, more than half of the commercially-available anti-HIV drugs are reverse transcriptase inhibitors (RTIs).

In the prior art, non-nucleoside reverse transcriptase inhibitors (NNRTIs) play an important role in the clinical treatment of AIDS and have become a major part of highly active anti-retroviral therapy (HAART) due to their high efficiency against the HIV-1 and low toxicity. By the end of 2019, more than 50 types of HIV-1 NNRTIs with different chemical structures have been discovered, of which six have been approved by Food and Drug Administration (FDA) for treatment of the AIDS, respectively nevirapine (NVP), delavirdine (DLV), efavirenz (EFV), etravirine (ETR), rilpivirine (RPV) and doravirine (DOR). In addition, the NNRTIs currently used in the clinical treatment are mainly the second-generation HIV NNRTIs, respectively diarylpyrimidine compounds, rilpivirine (RPV) and etravirine (ETR). However, in addition to the rapid emergence of virus mutant strains, these compounds themselves also struggle with poor water solubility (ETR, <<1 μg/mL; RPV, 20 ng/mL) and side effects in the long-term use, which greatly limit their clinical application. Therefore, there is an urgent need to develop a new and high-efficiency NNRTI with broad-spectrum antiviral activity and excellent pharmacokinetic properties.

SUMMARY

An object of this application is to provide a biphenyl diaryl pyrimidine derivative with an aromatic heterocyclic structure to overcome the defects in the prior art.

Technical solutions of this application are described as follows.

In a first aspect, this application provides a compound of formula (I) or a pharmaceutically-acceptable salt, a stereoisomer, a hydrate or a solvate thereof:

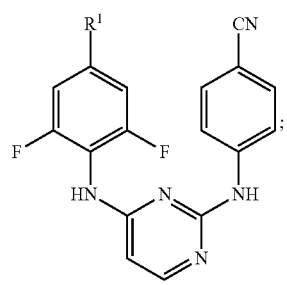

wherein $R^1$ is selected from the group consisting of substituted and unsubstituted furyl, substituted and unsubstituted thienyl, substituted and unsubstituted pyrazolyl, substituted and unsubstituted imidazolyl, substituted and unsubstituted thiazolyl, substituted and unsubstituted pyridyl, substituted and unsubstituted pyrimidinyl, substituted and unsubstituted p-aminophenyl and substituted and unsubstituted $C_7$-$C_{10}$ aromatic heterocyclic group.

In an embodiment, the compound is selected from the group consisting of

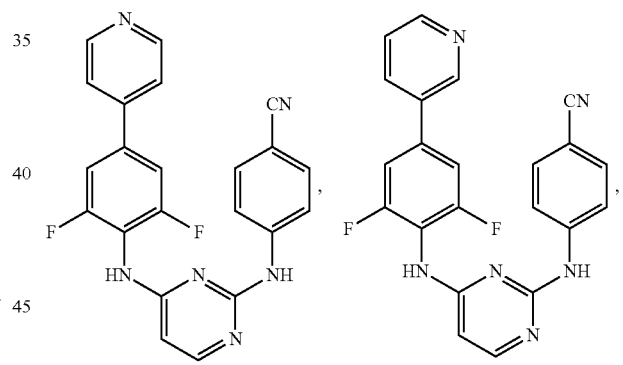

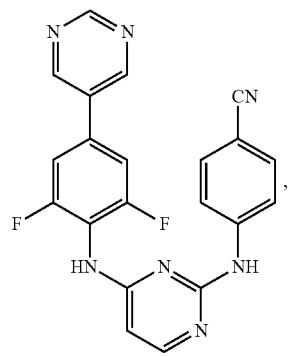

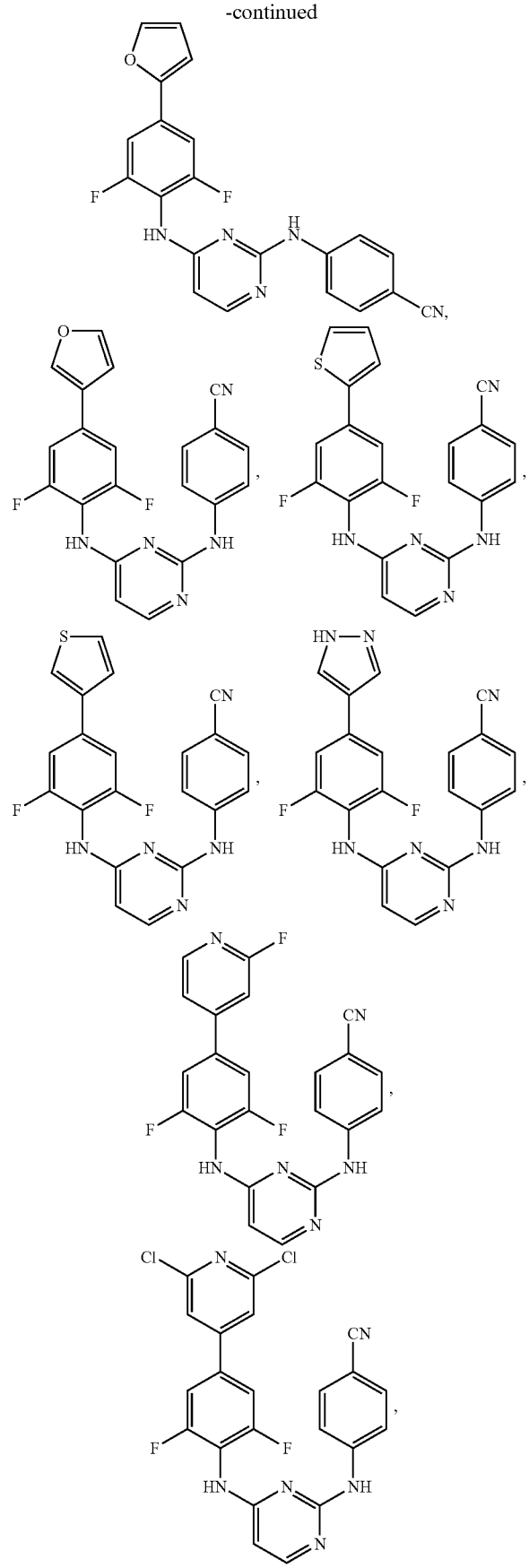
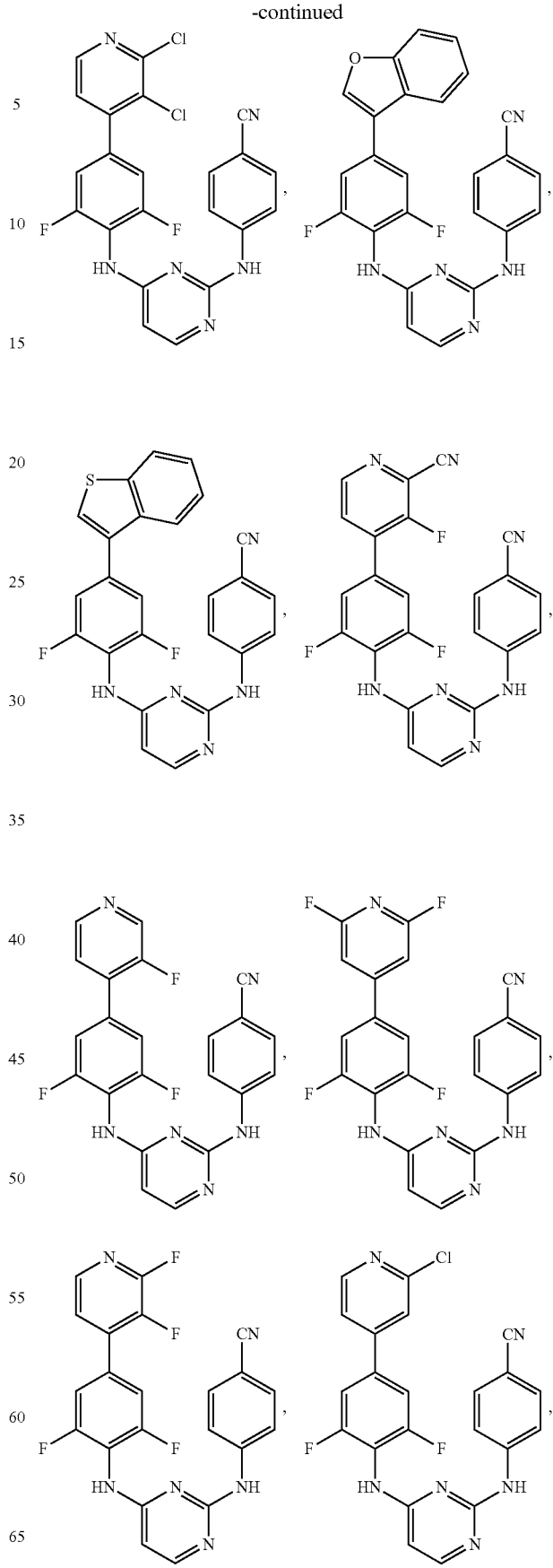

-continued

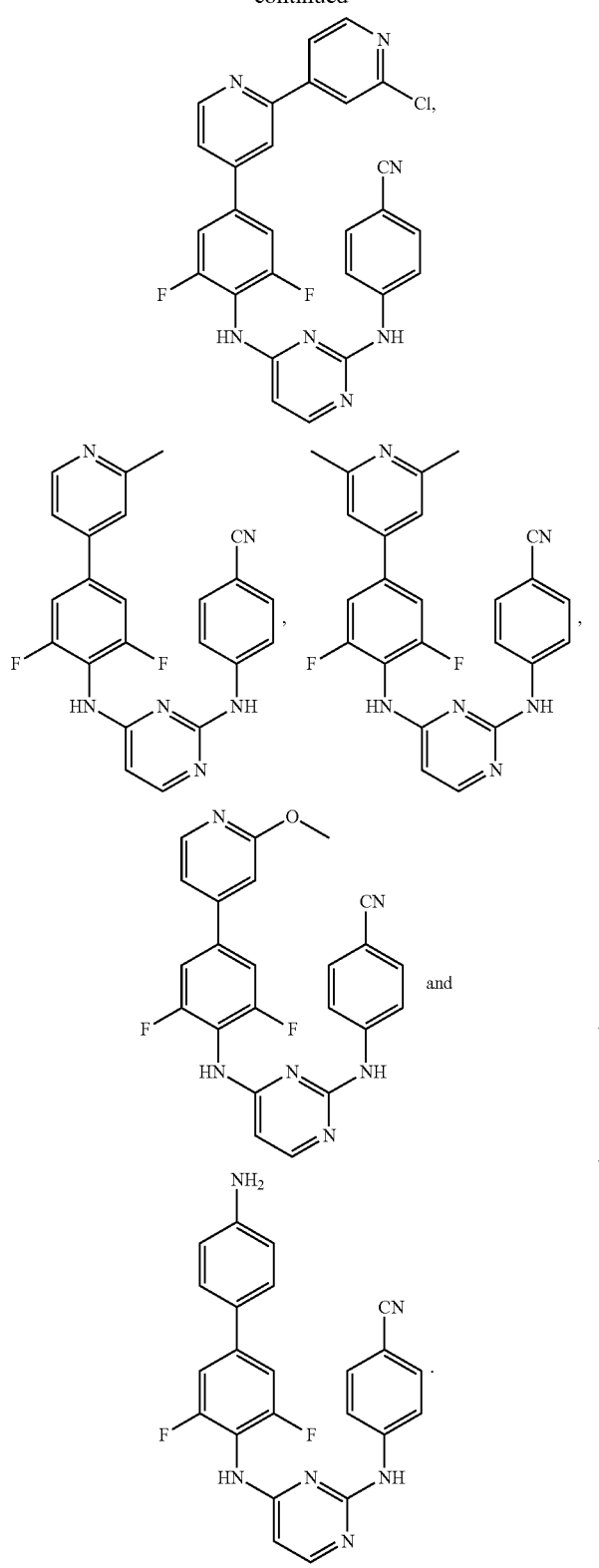

In an embodiment, the pharmaceutically-acceptable salt is selected from the group consisting of hydrochloride, hydrobromide, formate, methanesulfonate, trifluoromethanesulfonate, sulfate, phosphate, acetate, p-toluenesulfonate, tartrate, citrate, succinate, maleate, fumarate and malate.

In a second aspect, this application further provides a method of preparing the compound of formula (I), comprising:

subjecting a compound of formula (II) and a heterocyclic boronic acid to Suzuki cross-coupling reaction in a solvent in the presence of Pd(dppf)Cl$_2$ and Cs$_2$CO$_3$ to obtain the compound of formula (I), as shown in the following scheme:

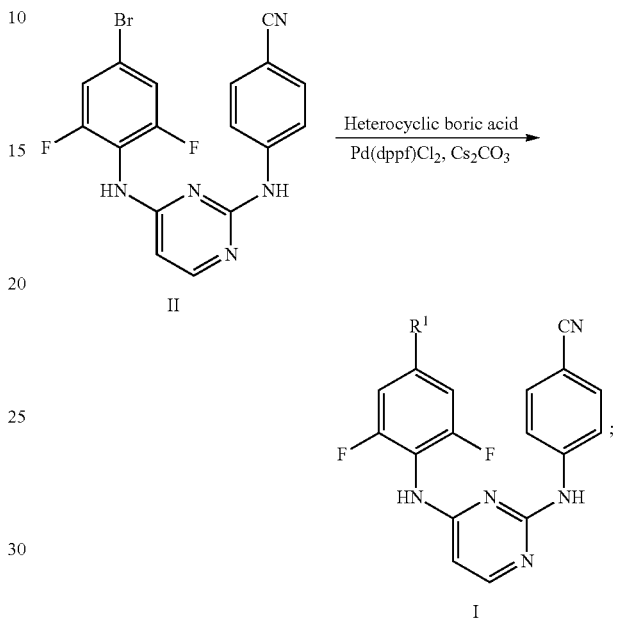

wherein R$^1$ is selected from the group consisting of substituted and unsubstituted furyl, substituted and unsubstituted thienyl, substituted and unsubstituted pyrazolyl, substituted or unsubstituted imidazolyl, substituted and unsubstituted thiazolyl, substituted and unsubstituted pyridyl, substituted and unsubstituted pyrimidinyl, substituted and unsubstituted p-aminophenyl and substituted and unsubstituted C$_7$-C$_{10}$ aromatic heterocyclic group.

In an embodiment, the solvent is selected from the group consisting of methanol, ethanol, n-propanol, isopropyl alcohol, n-butanol, tert-butanol, dichloromethane, dichloroethane, toluene, tetrahydrofuran, diethyl ether, isopropyl ether, methyl tert-butyl ether, 1, 4-dioxane, ethyl acetate and a combination thereof.

In an embodiment, the heterocyclic boronic acid is selected from the group consisting of 4-pyridyl boronic acid, 3-pyridyl boronic acid, 5-pyrimidyl boronic acid, 2-furyl boronic acid, 3-furyl boronic acid, 2-thienyl boronic acid, 3-thienyl boronic acid, 4-imidazolyl boronic acid, 2-fluoro-4-pyridyl boronic acid, 2,6-dichloro-4-pyridyl boronic acid, 2,3-dichloro-4-pyridyl boronic acid, 3-benzofuryl boronic acid, 3-benzothienyl boronic acid, 3-fluoro-2-cyano-4-pyridyl boronic acid, 3-fluoro-4-pyridyl boronic acid, 2,6-difluoro-4-pyridyl boronic acid, 2,3-difluoro-4-pyridyl boronic acid, 2-fluoro-4-pyridyl boronic acid, dipyridylboronic acid, 2-methyl-4-pyridyl boronic acid, 2,6-dimethyl-4-pyridyl boronic acid, 2-methoxy-4-pyridyl boronic acid, p-aminophenylboronic acid and a combination thereof.

In an embodiment, a molar ratio of the compound of formula (II) to the heterocyclic boronic acid is 1:(1-8).

In an embodiment, a molar ratio of the compound of formula (II) to the Pd(dppf)Cl$_2$ is 1:(0.01-0.10).

In an embodiment, a molar ratio of the compound of formula (II) to the Cs₂CO₃ is 1:(1-2).

In an embodiment, a reaction temperature is 40-180° C.

In an embodiment, the reaction temperature is 80-170° C.

In an embodiment, a reaction time is 4-24 h.

In a third aspect, this application further provides a pharmaceutical composition, comprising a pharmaceutically effective amount of the above-mentioned compound or the pharmaceutically-acceptable salt, the stereoisomer, the hydrate or the solvate thereof and a pharmaceutically-acceptable carrier.

In an embodiment, the pharmaceutical composition comprises a pharmaceutically effective amount of the above-mentioned compound or the pharmaceutically-acceptable salt, the stereoisomer, the hydrate or the solvate thereof and the pharmaceutically-acceptable carrier.

In a fourth aspect, this application further provides a method for treating acquired immune deficiency syndrome (AIDS) in a patient in need thereof, comprising: administering a therapeutically effective amount of the pharmaceutical composition to the patient.

In a fifth aspect, this application further provides a compound of formula (I), or a polycrystal, a eutectic or a single-enantiomer X-ray diffraction single crystal thereof:

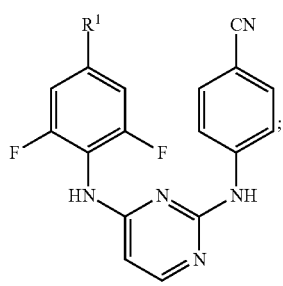

I wherein R¹ is selected from the group consisting of substituted and unsubstituted furyl, substituted and unsubstituted thienyl, substituted and unsubstituted pyrazolyl, substituted and unsubstituted imidazolyl, substituted and unsubstituted thiazolyl, substituted and unsubstituted pyridyl, substituted and unsubstituted pyrimidinyl, substituted and unsubstituted p-aminophenyl and substituted and unsubstituted $C_7$-$C_{10}$ aromatic heterocyclic group.

In an embodiment, the compound is selected from the group consisting

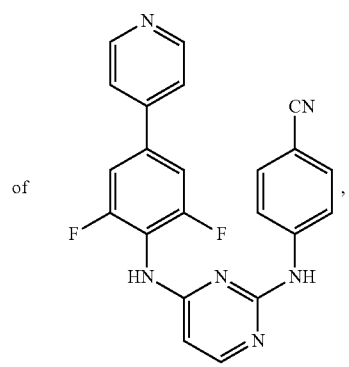

of,

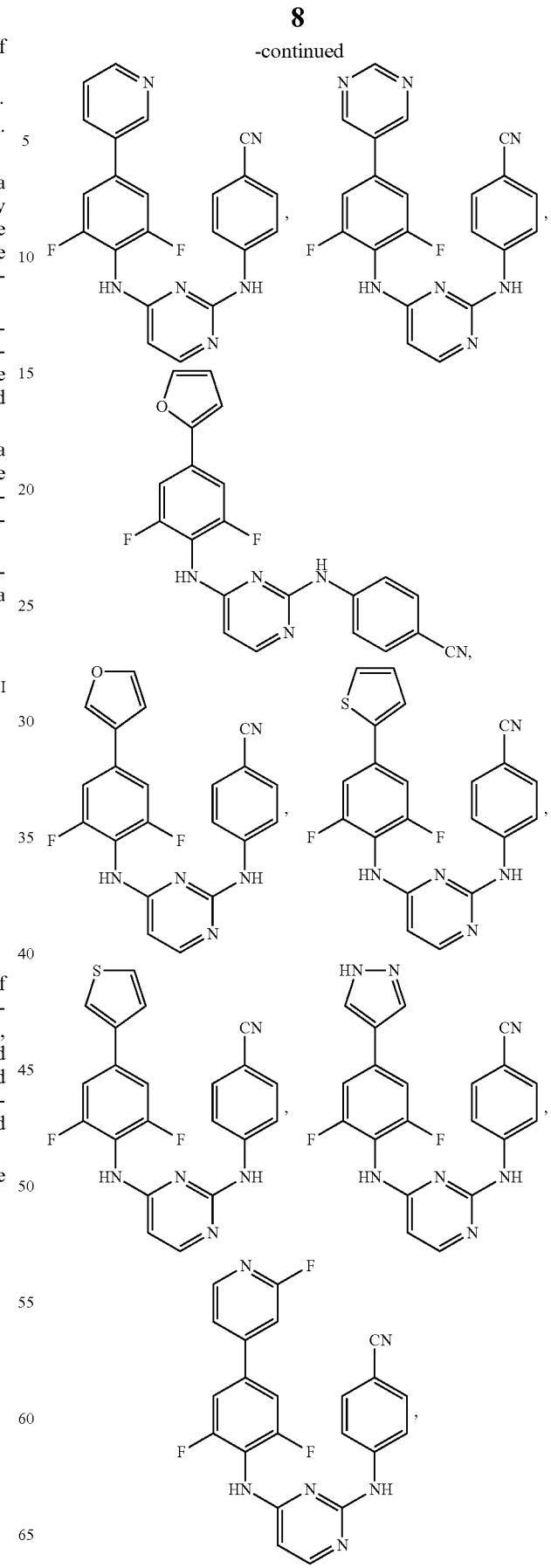

-continued
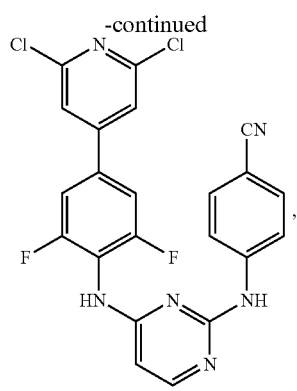
,
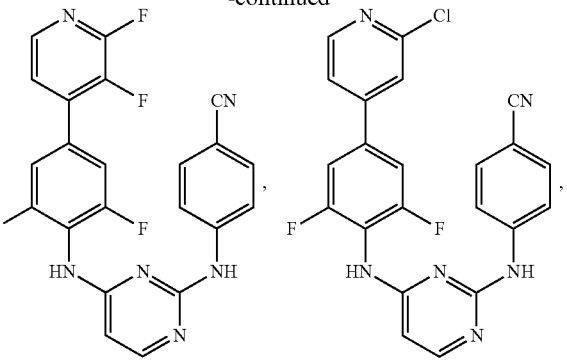
,
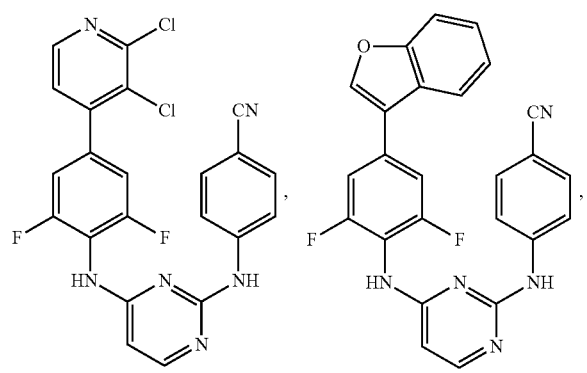
,
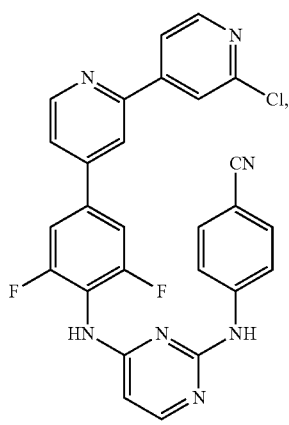
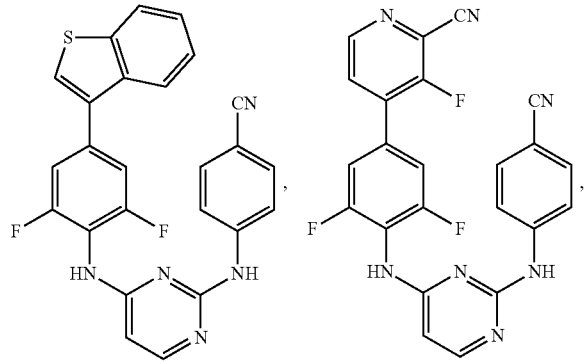
,
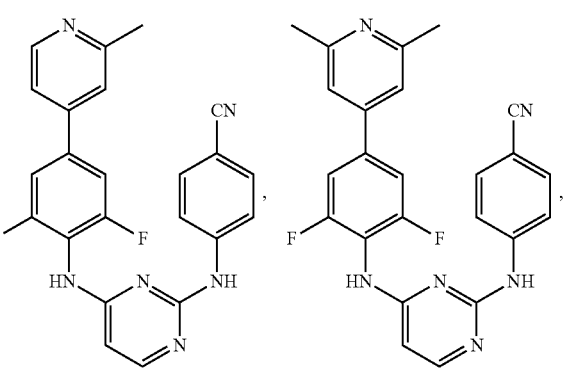
,
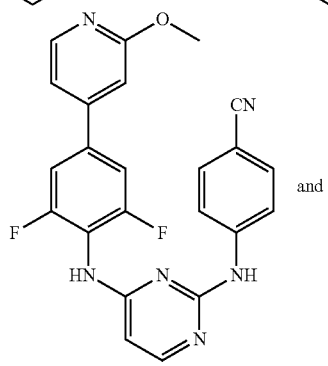 and -continued

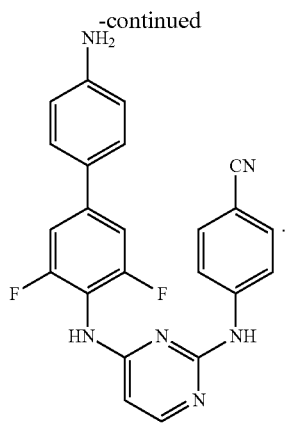

In an embodiment, a pharmaceutically-acceptable salt is selected from a group consisting of hydrochloride, hydrobromide, formate, methanesulfonate, trifluoromethanesulfonate, sulfate, phosphate, acetate, p-toluenesulfonate, tartrate, citrate, succinate, maleate, fumarate or malate.

In a sixth aspect, this application further provides a pharmaceutical composition, comprising the compound, or the polycrystal, the eutectic or the single-enantiomer X-ray diffraction single crystal thereof, and a pharmaceutically-acceptable carrier.

In an embodiment, the pharmaceutical composition comprises a pharmaceutically effective amount of the compound, or the polycrystal, the eutectic or the single-enantiomer X-ray diffraction single crystal thereof, and the pharmaceutically-acceptable carrier.

In a seventh aspect, this application further provides a method for treating AIDS in a patient in need thereof, comprising administering a therapeutically effective amount of the pharmaceutical composition to the patient.

DETAILED DESCRIPTION OF EMBODIMENTS

This application optimizes a structure of a diarylpyrimidine non-nucleoside reverse transcriptase inhibitor (NNRTI) and the salt-formation thereof, and also investigates the pharmacological and toxicological properties to obtain a novel and effective NNRTI with excellent antiviral activity and pharmacokinetic property.

This application replaces a p-cyanophenyl fragment in a biphenyl fragment of a difluorobiphenyl diarylpyrimidine inhibitor with an aromatic heterocyclic fragment by using a classical bioisosterism strategy in combination with computer-aided drug design based on a binding mode between a biphenyl diaryl pyrimidine derivative with an aromatic heterocyclic structure and HIV reverse transcriptase to retain a π-π stacking interaction between the original compound and aromatic amino acid residues Y181 and Y188 in a binding pocket. At the same time, heteroatoms are introduced to improve the molecular water solubility and drug-gability parameters of the inhibitor molecule. In addition, the central pyrimidine mother ring can still form hydrogen bonds with amino acid residues E138 and K101 in the optimized molecular skeleton, so as to stabilize the binding conformation, further enhancing the biological activity of the optimized compound against HIV strains. Results of the in-vitro test show that the optimized compound has significant anti-HIV-1 activity and a relatively low cytotoxicity. At the same time, the pharmaceutically-acceptable salt of the optimized compound is demonstrated by solubility test to have excellent water solubility in a wide pH range, having a good clinical application prospect.

This application will be further described in detail with reference to the embodiments, but is not limited thereto.

Example 1 Preparation of Target Compound (Ia)

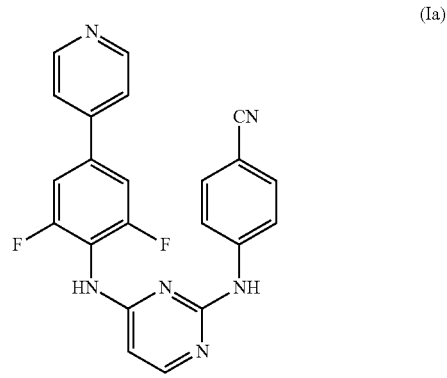 [SMILES: N#Cc1ccc(Nc2nccc(Nc3c(F)cc(-c4ccncc4)cc3F)n2)cc1]

(Ia)

1.0 mmol of 4-((4-((4-bromo-2,6-difluorophenyl)(methyl) amino) pyrimidin-2-yl) amino) benzenonitrile, 1.0 mmol of cesium carbonate, 0.01 mmol of Pd(dppf)Cl$_2$ and 1.2 mmol of 4-pyridyl boronic acid were added to 6 mL of 1,4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ia) (yield: 75%; melting point: 287.1-288.1° C.).

The target compound (Ia) was characterized as follows.

$^1$H NMR (400 MHz, DMSO-d$_6$) δ: 9.76 (s, 1H, NH), 9.41 (s, 1H, NH), 8.70 (m, 2H, ArH), 8.14 (d, J=4 Hz, 1H, pyrimidine-H), 7.87-7.83 (m, 4H, ArH), 7.65 (dd, J=8.0 Hz, J=100 Hz 4H, ArH), 6.36 (d, J=4.0 Hz, 1H, pyrimidine-H).

$^{13}$C NMR (100 MHz, DMSO-d$_6$) δ: 161.8, 160.1-157.6 (dd, $J_{C-F}$=6 Hz, $J_{C-F}$=242 Hz), 157.2, 150.9, 145.7, 136.7 (t, $J_{C-F}$=11 Hz), 133.1, 121.6, 120.1, 118.5, 117.0, 111.1, 110.9, 102.1, 99.4.

HRMS (ESI$^+$): m/z calcd for $C_{22}H_{14}F_2N_6$ [M+Na]$^+$ 400.1248, found 423.1140. HPLC: $t_R$=11.010 min, 99.09%, (λ=254 nm).

Example 2 Preparation of Target Compound (Ib)

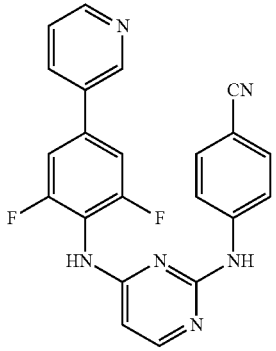

(Ib)

1.0 mmol of 4-((4-((4-bromo-2,6-difluorophenyl)(methyl) amino) pyrimidin-2-yl) amino) benzenonitrile, 2.0 mmol of cesium carbonate, 0.01 mmol of Pd(dppf)Cl$_2$ and 1.2 mmol of 3-pyridyl boronic acid were added to 5 mL of 1,4-dioxane at room temperature. After the atmosphere in the reaction system was replaced with nitrogen three times, the reaction mixture was reacted under stirring at 150° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ib) (yield: 82%; melting point: 232.2-232.9° C.).

The target compound (Ib) was characterized as follows.

$^1$H NMR (400 MHz, DMSO-d$_6$) δ: 9.77 (s, 1H, NH), 9.36 (s, 1H, NH), 9.07 (m, 1H, ArH), 8.65 (d, J=4 Hz, 1H, pyrimidine-H), 8.26-8.23 (m, 1H, ArH), 8.14 (d, J=4 Hz, 1H, ArH), 7.81-7.76 (m, 4H, ArH), 7.56-7.52 (m, 3H, ArH), 6.36 (d, J=4.0 Hz, 1H, pyrimidine-H).

$^{13}$C NMR (100 MHz, DMSO-d$_6$) δ: 162.0, 160.2-157.7 (dd, J$_{C-F}$=6 Hz, J$_{C-F}$=240 Hz), 159.6, 157.1, 149.9, 148.2, 145.7, 136.9 (t, J$_{C-F}$=10 Hz), 134.7, 133.1, 124.4, 120.1, 118.5, 115.9 (t, J$_{C-F}$=16 Hz), 111.0, 110.8, 102.1, 99.3.

HRMS (ESI$^+$): m/z calcd for C$_{22}$H$_{14}$F$_2$N$_6$ [M+Na]$^+$ 400.12481, found 423.1147. HPLC: t$_R$=0.707 min, 99.51%, (λ=254 nm).

Example 3 Preparation of Target Compound (Ic)

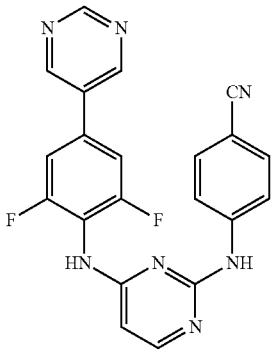

(Ic)

1.0 mmol of 4-((4-((4-bromo-2,6-difluorophenyl)(methyl) amino) pyrimidin-2-yl) amino) benzenonitrile, 2.0 mmol of cesium carbonate, 0.01 mmol of Pd(dppf)Cl$_2$ and 1.0 mmol of 5-pyrimidyl boronic acid were added to 6 mL of 1,4-dioxane at room temperature. After the atmosphere in the reaction system was replaced with nitrogen three times, the reaction mixture was reacted under stirring at 80° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ic) (yield: 95%; melting point: 256.8-257.2° C.).

The target compound (Ic) was characterized as follows.

$^1$H NMR (400 MHz, DMSO-d$_6$) δ: 9.74 (s, 1H, NH), 9.37 (s, 1H, NH), 9.29 (s, 2H, ArH), 9.24 (s, 1H, ArH), 8.12 (d, J=4 Hz, 1H, pyrimidine-H), 7.82 (dd, J=8 Hz, J=28 Hz, 4H, ArH), 7.53 (d, J=8 Hz, 2H, ArH), 6.35 (d, J=8.0 Hz, 1H, pyrimidine-H).

$^{13}$C NMR (100 MHz, DMSO-d$_6$) δ: 161.8, 160.1-157.6 (dd, J$_{C-F}$=6 Hz, J$_{C-F}$=240 Hz), 159.6, 158.4, 157.2, 155.4, 145.6, 133.2, 131.3, 120.1, 118.5, 116.7 (t, J$_{C-F}$=18 Hz), 111.2, 111.0, 102.2, 99.4.

HRMS (ESI$^+$): m/z calcd for C$_{21}$H$_{13}$F$_2$N$_7$ [M+Na]$^+$ 401.1200, found 424.1103. HPLC: t$_R$=4.22 min, 95.20%, (λ=254 nm).

Example 4 Preparation of Target Compound (Id)

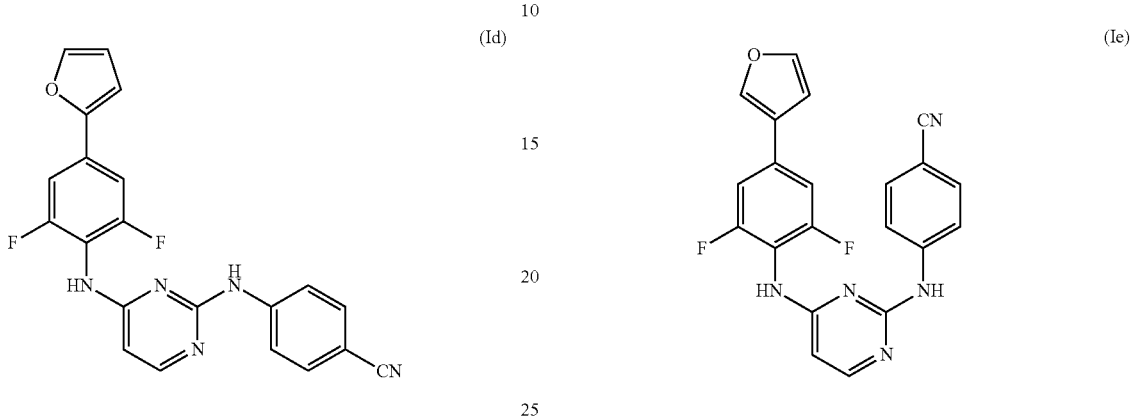

1.0 mmol of 4-((4-((4-bromo-2,6-difluorophenyl)(methyl) amino) pyrimidin-2-yl) amino) benzenonitrile, 2.0 mmol of cesium carbonate, 0.01 mmol of Pd(dppf)Cl$_2$ and 8.0 mmol of 2-furyl boronic acid were added to 6 mL of toluene at room temperature. After the atmosphere in the reaction system was replaced with nitrogen three times, the reaction mixture was reacted under stirring at 100° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Id) (yield: 92%; melting point: 205.4-205.9° C.).

The target compound (Id) was characterized as follows.

$^1$H NMR (400 MHz, DMSO-d$_6$) δ: 9.77 (s, 1H, NH), 9.29 (s, 1H, NH), 8.11 (d, J=4 Hz, 1H, pyrimidine-H), 7.83 (s, 1H, ArH), 7.60 (d, J=8 Hz, 2H, ArH), 7.82-7.49 (dd, J=12 Hz, J=112 Hz, 4H, ArH), 7.20 (d, J=4.0 Hz, 1H), 6.67 (s, 1H, ArH), 6.34 (d, J=4 Hz, 1H, pyrimidine-H).

$^{13}$C NMR (100 MHz, DMSO-d$_6$) δ: 162.0, 160.2-157.7 (dd, J$_{C-F}$=6 Hz, J$_{C-F}$=239 Hz), 159.5, 157.1, 151.3, 145.8, 144.5, 133.0, 130.1 (t, J$_{C-F}$=10 Hz), 120.1, 118.5, 115.0 (t, J$_{C-F}$=17 Hz), 113.0, 108.7, 107.5, 107.2, 102.1, 99.2.

HRMS (ESI$^+$): m/z calcd for C$_{21}$H$_{13}$F$_2$N$_5$O [M+H]$^+$ 389.1088, found 390.1161. HPLC: t$_R$=5.85 min, 99.36%, (λ=254 nm).

Example 5 Preparation of Target Compound (Ie)

1.0 mmol of 4-((4-((4-bromo-2,6-difluorophenyl)(methyl) amino) pyrimidin-2-yl) amino) benzenonitrile, 2.0 mmol of cesium carbonate, 0.01 mmol of Pd(dppf)Cl$_2$ and 8.0 mmol of 3-furyl boronic acid were added to 6 mL of methanol at room temperature. After the atmosphere in the reaction system was replaced with nitrogen three times, the reaction mixture was reacted under stirring at 110° C. for 24 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ie) (yield: 89%; melting point: 191.7-192.4° C.).

The target compound (Ie) was characterized as follows.

$^1$H NMR (400 MHz, DMSO-d$_6$) δ: 9.78 (s, 1H, NH), 9.26 (s, 1H, NH), 8.41 (s, 1H, ArH), 8.14-8.12 (m, 1H, ArH), 7.84-7.78 (m, 3H, ArH), 7.64-7.50 (m, 4H, ArH), 7.13 (d, J=4.0 Hz, 1H), 6.35 (s, 1H, ArH).

$^{13}$C NMR (100 MHz, DMSO-d$_6$) δ: 162.2, 160.3-157.0 (dd, J$_{C-F}$=7 Hz, J$_{C-F}$=239 Hz), 159.6, 157.0, 145.8, 145.1, 141.2, 133.0, 132.4 (t, J$_{C-F}$=11 Hz), 124.7, 120.1, 118.5, 114.4 (t, J$_{C-F}$=17 Hz), 109.4 (d, J$_{C-F}$=24 Hz), 109.1, 102.2, 99.2.

HRMS (ESI$^+$): m/z calcd for C$_{21}$H$_{13}$F$_2$N$_5$O [M+H]$^+$ 389.1088, found 390.1159. HPLC: t$_R$=5.32 min, 97.95%, (λ=254 nm).

Example 6 Preparation of Target Compound (If)

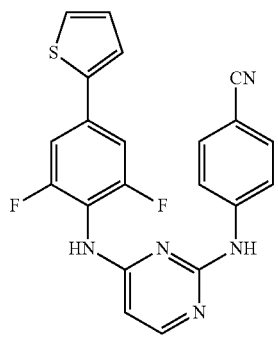
(If)

1.0 mmol of 4-((4-((4-bromo-2,6-difluorophenyl)(methyl) amino) pyrimidin-2-yl) amino) benzenonitrile, 4.0 mmol of cesium carbonate, 0.01 mmol of Pd(dppf)Cl$_2$ and 4.0 mmol of 2-thienyl boronic acid were added to 6 mL of 1, 4-dioxane at room temperature. After the atmosphere in the reaction system was replaced with nitrogen three times, the reaction mixture was reacted under stirring at 110° C. for 14 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (If) (yield: 95%; melting point: 259.8-260.2° C.).

The target compound (If) was characterized as follows.

$^1$H NMR (400 MHz, DMSO-d$_6$) δ: 9.72 (s, 1H, NH), 9.26 (s, 1H, NH), 8.10 (d, J=4 Hz, 1H, pyrimidine-H), 7.77 (d, J=8 Hz, 2H, ArH), 7.74 (dd, J=4 Hz, J=16 Hz, 2H, ArH), 7.58 (d, J=8.0 Hz, 2H), 7.48 (d, J=8.0 Hz, 2H), 7.19 (t, J=4.0 Hz, 1H, ArH) 6.32 (d, J=4 Hz, 1H, pyrimidine-H).

$^{13}$C NMR (100 MHz, DMSO-d$_6$) δ: 162.0, 160.2-157.7 (dd, J$_{C-F}$=6 Hz, J$_{C-F}$=241 Hz), 159.5, 157.1, 145.8, 141.1, 133.0, 129.3, 127.8, 126.1, 120.1, 118.5, 115.0 (t, J$_{C-F}$=17 Hz), 109.5, 109.2, 102.1, 99.2.

HRMS (ESI$^+$): m/z calcd for C$_{21}$H$_{13}$F$_2$N$_5$S [M+H]$^+$ 405.0860, found 406.0919. HPLC: t$_R$=7.48 min, 98.11%, (λ=254 nm).

Example 7 Preparation of Target Compound (Ig)

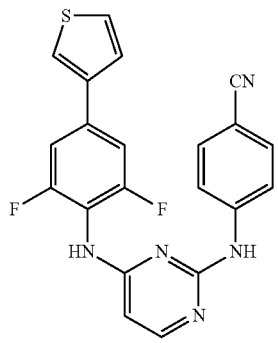
(Ig)

1.0 mmol of 4-((4-((4-bromo-2,6-difluorophenyl)(methyl) amino) pyrimidin-2-yl) amino) benzenonitrile, 4.0 mmol of cesium carbonate, 0.05 mmol of Pd(dppf)Cl$_2$ and 4.0 mmol of 3-thienyl boronic acid were added to 6 mL of 1, 4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ig) (yield: 82%; melting point: 220.0-221.0° C.).

The target compound (Ig) was characterized as follows.

$^1$H NMR (400 MHz, DMSO-d$_6$) δ: 9.72 (s, 1H, NH), 9.23 (s, 1H, NH), 8.13 (m, 1H, ArH), 8.10 (d, J=4 Hz, 1H, pyrimidine-H), 7.72-7.68 (m, 4H, ArH), 7.79-7.47 (dd, J=8 Hz, J=112 Hz, 4H, ArH), 6.31 (d, J=4 Hz, 1H, pyrimidine-H).

$^{13}$C NMR (100 MHz, DMSO-d$_6$) δ: 162.1, 160.2-157.8 (dd, J$_{C-F}$=6 Hz, J$_{C-F}$=241 Hz), 159.6, 145.8, 139.5, 135.2, 133.1, 128.1, 126.7, 123.4, 120.1, 118.5, 114.6 (t, J$_{C-F}$=15 Hz), 110.0, 109.8, 102.1, 99.2.

HRMS (ESI$^+$): m/z calcd for C$_{21}$H$_{13}$F$_2$N$_5$S [M+H]$^+$ 405.0860, found 406.0935. HPLC: t$_R$=7.19 min, 97.26%, (λ=254 nm).

Example 8 Preparation of Target Compound (Ih)

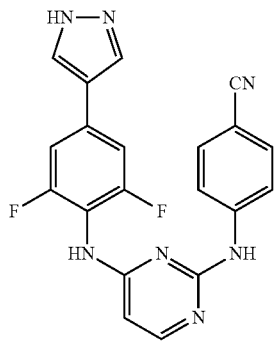

(Ih)

1.0 mmol of 4-((4-((4-bromo-2,6-difluorophenyl)(methyl) amino) pyrimidin-2-yl) amino) benzenonitrile, 4.0 mmol of cesium carbonate, 0.08 mmol of Pd(dppf)Cl$_2$ and 8.0 mmol of 4-imidazolyl boronic acid were added to 6 mL of 1, 4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ih) (yield: 52%; melting point: 273.4-274.1° C.).

The target compound (Ih) was characterized as follows.

$^1$H NMR (400 MHz, DMSO-d$_6$) δ: 13.11 (s, 1H, pyrazole-H), 9.72 (s, 1H, NH), 9.16 (s, 1H, NH), 8.41 (s, 1H, pyrazole-H), 8.12-8.09 (m, 2H, ArH), 7.80-7.48 (dd, J=8.0 Hz, J=112 Hz, 4H, ArH), 7.58 (d, J=8.0 Hz, 2H, ArH), 6.30 (m, 1H, pyrimidine-H).

$^{13}$C NMR (100 MHz, DMSO-d$_6$) δ: 162.3, 160.4-157.9 (dd, $J_{C-F}$=6 Hz, $J_{C-F}$=238 Hz), 159.6, 157.0, 145.7, 137.2, 133.6 (t, $J_{C-F}$=9 Hz), 133.0, 127.0, 120.1, 119.9 (t, $J_{C-F}$=3 Hz), 118.5, 113.1 (t, $J_{C-F}$=17 Hz), 108.9 (d, $J_{C-F}$=24 Hz), 102.0.

HRMS (ESI$^+$): m/z calcd for C$_{20}$H$_{13}$F$_2$N$_7$ [M+Na]$^+$ 389.1200, found 412.1092.

HPLC: $t_R$=4.206 min, 96.01%, (λ=254 nm).

Example 9 Preparation of Target Compound (Ii)

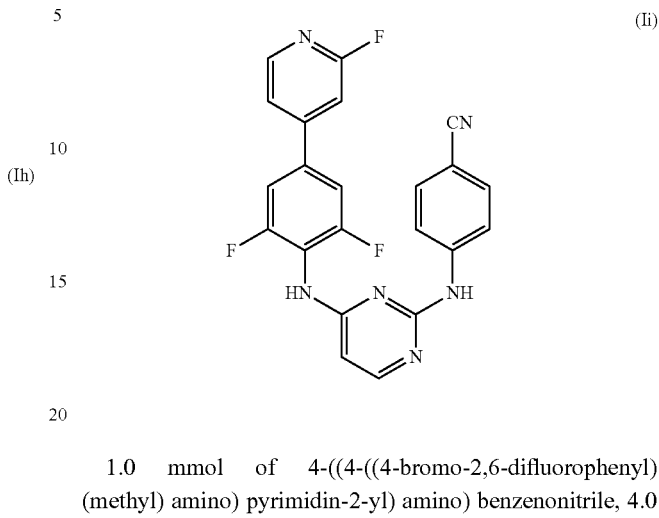

(Ii)

1.0 mmol of 4-((4-((4-bromo-2,6-difluorophenyl)(methyl) amino) pyrimidin-2-yl) amino) benzenonitrile, 4.0 mmol of cesium carbonate, 0.01 mmol of Pd(dppf)Cl$_2$ and 1.2 mmol of 2-fluoro-4-pyridyl boronic acid were added to 6 mL of 1, 4-dioxane at room temperature. After the atmosphere in the reaction system was replaced with nitrogen three times, the reaction mixture was reacted under stirring at 100° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ii) (yield: 82%; melting point: 259.0-260.0° C.).

The target compound (Ii) was characterized as follows.

$^1$H NMR (400 MHz, DMSO-d$_6$) δ: 9.75 (s, 1H, NH), 9.44 (s, 1H, NH), 8.38 (d, J=8 Hz, 1H, ArH), 8.14 (d, J=4 Hz, 1H, pyrimidine-H), 7.92 (d, J=12 Hz, 2H, ArH), 7.88 (d, J=4 Hz, 1H, ArH), 7.79-7.52 (dd, J=8.0 Hz, J=92 Hz, 4H, ArH), 7.74 (s, 1H, ArH), 6.38 (d, J=8 Hz, 1H, pyrimidine-H).

$^{13}$C NMR (100 MHz, DMSO-d$_6$) δ: 165.8-163.5 (d, $J_{C-F}$=219 Hz), 161.7, 159.9-157.4 (dd, $J_{C-F}$=6 Hz, $J_{C-F}$=240 Hz), 159.5, 157.2, 150.7 (d, $J_{C-F}$=8 Hz), 148.8 (d, $J_{C-F}$=15 Hz), 145.7, 135.3 (t, $J_{C-F}$=11 Hz), 133.1, 120.1, 119.9 (d, $J_{C-F}$=4 Hz), 118.5, 117.7 (t, $J_{C-F}$=16 Hz), 111.5-111.3 (dd, $J_{C-F}$=6 Hz, $J_{C-F}$=13 Hz), 107.5-107.1 (d, $J_{C-F}$=39 Hz), 102.2, 99.4.

HRMS (ESI$^+$): m/z calcd for C$_{22}$H$_{13}$F$_3$N$_6$ [M+Na]$^+$ 418.1154, found 441.1042. HPLC: $t_R$=5.73 min, 97.47%, (λ=254 nm).

Example 10 Preparation of Target Compound (Ij)

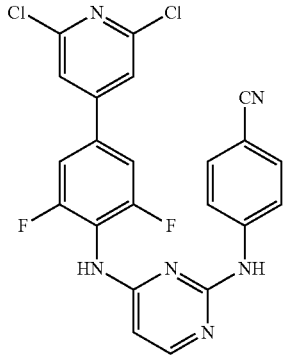

1.0 mmol of 4-((4-((4-bromo-2,6-difluorophenyl)(methyl) amino) pyrimidin-2-yl) amino) benzenonitrile, 4.0 mmol of cesium carbonate, 0.01 mmol of Pd(dppf)Cl$_2$ and 1.2 mmol of 2,6-dichloro-4-pyridyl boronic acid were added to 6 mL of methanol at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ij) (yield: 96%; melting point: 205.3-205.9° C.).

The target compound (Ij) was characterized as follows.

$^1$H NMR (400 MHz, DMSO-d$_6$) δ: 9.76 (s, 1H, NH), 9.47 (s, 1H, NH), 8.56 (d, J=8 Hz, 1H, pyrimidine-H), 8.37-8.08 (m, 5H, ArH), 7.95 (d, J=8 Hz, 1H, ArH), 7.78-7.52 (dd, J=8.0 Hz, J=88 Hz, 4H, ArH), 6.38 (d, J=4 Hz, 1H, pyrimidine-H).

$^{13}$C NMR (100 MHz, DMSO-d$_6$) δ: 161.6, 159.8-159.7 (d, J$_{C-F}$=6 Hz), 159.5, 157.3, 150.7, 145.6, 133.6 (t, J$_{C-F}$=10 Hz), 133.1, 123.1, 121.2, 120.1, 118.5, 118.3 (t, J$_{C-F}$=16 Hz), 111.9-111.7 (dd, J$_{C-F}$=25 Hz), 102.2, 99.5.

HRMS (ESI$^+$): m/z calcd for C$_{22}$H$_{12}$C$_{12}$F$_2$N$_6$ [M+Na]$^+$ 468.0469, found 491.0366. HPLC: t$_R$=7.59 min, 98.31%, (λ=254 nm).

Example 11 Preparation of Target Compound (Ik)

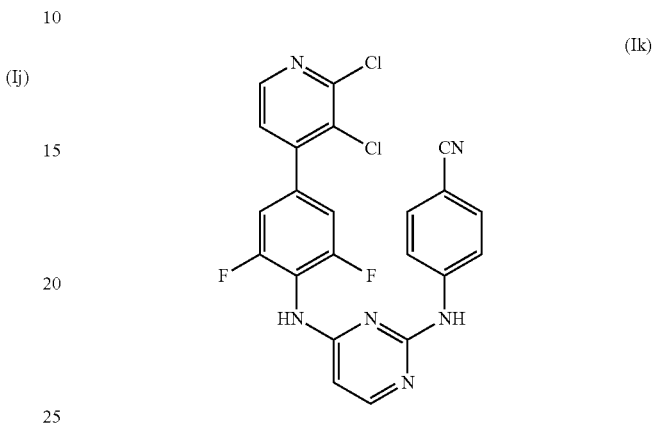

1.0 mmol of 4-((4-((4-bromo-2,6-difluorophenyl)(methyl) amino) pyrimidin-2-yl) amino) benzenonitrile, 4.0 mmol of cesium carbonate, 0.08 mmol of Pd(dppf)Cl$_2$ and 1.2 mmol of 2, 3-dichloro-4-pyridyl boronic acid were added to 6 mL of 1, 4-dioxane at room temperature. After the atmosphere in the reaction system was replaced with nitrogen three times, the reaction mixture was reacted under stirring at 170° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ik) (yield: 88%; melting point: 268.1-268.7° C.).

The target compound (Ik) was characterized as follows.

$^1$H NMR (400 MHz, DMSO-d$_6$) δ: 9.75 (s, 1H, NH), 9.45 (s, 1H, NH), 8.66-8.09 (m, 4H, ArH), 7.78-7.52 (dd, J=8.0 Hz, 4H, ArH), 7.97 (d, J=8.0 Hz, 1H, pyrimidine-H), 6.37 (d, J=4.0 Hz, 1H, pyrimidine-H).

$^{13}$C NMR (100 MHz, DMSO-d$_6$) δ: 161.7, 159.5, 159.1-156.6 (dd, J$_{C-F}$=6 Hz, J$_{C-F}$=241 Hz), 157.3, 149.5, 148.8, 148.0, 145.6, 135.3 (t, J$_{C-F}$=10 Hz), 133.1, 128.1, 125.9, 120.1, 118.5, 117.1 (t, J$_{C-F}$=17 Hz), 113.7-113.5 (dd, J$_{C-F}$=7 Hz, J$_{C-F}$=13 Hz), 102.2, 99.4.

HRMS (ESI$^+$): m/z calcd for C$_{22}$H$_{12}$C$_{12}$F$_2$N$_6$ [M+H]$^+$ 468.1510, found 469.0545. HPLC: t$_R$=7.39 min, 97.32%, (λ=254 nm).

Example 12 Preparation of Target Compound (Il)

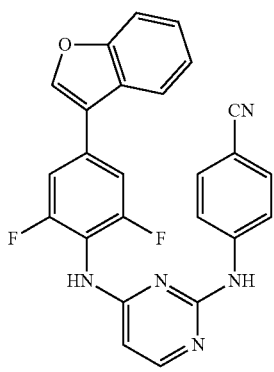

(Il)

1.0 mmol of 4-((4-((4-bromo-2,6-difluorophenyl)(methyl) amino) pyrimidin-2-yl) amino) benzonitrile, 4.0 mmol of cesium carbonate, 0.10 mmol of Pd(dppf)Cl$_2$ and 1.2 mmol of 3-benzofuryl boronic acid were added to 6 mL of 1,4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Il) (yield: 92%; melting point: 236.2-236.9° C.).

The target compound (Il) was characterized as follows.

$^1$H NMR (400 MHz, DMSO-d$_6$) δ: 9.76 (s, 1H, NH), 9.33 (s, 1H, NH), 8.61 (s, 1H, ArH), 8.15 (d, J=4 Hz, 1H, pyrimidine-H), 8.05 (d, J=8 Hz, 1H, ArH), 7.82-7.52 (dd, J=8.0 Hz, J=104 Hz, 4H, ArH), 7.74-7.68 (m, 3H, ArH), 7.48-7.40 (m, 2H, ArH), 6.37 (d, J=4.0 Hz, 1H, pyrimidine-H).

$^{13}$C NMR (100 MHz, DMSO-d$_6$) δ: 162.1, 159.6, 160.2-157.7 (dd, J$_{C-F}$=7 Hz, J$_{C-F}$=239 Hz), 157.1, 155.7, 145.8, 144.7, 133.1, 131.6 (t, J$_{C-F}$=10 Hz), 125.6, 125.3, 124.2, 120.8, 120.1, 119.8, 118.5, 115.1 (t, J$_{C-F}$=16 Hz), 112.4, 111.0-110.7 (d, J$_{C-F}$=25 Hz), 102.1, 99.2.

HRMS (ESI$^+$): m/z calcd for C$_{25}$H$_{15}$F$_2$N$_7$O [M+H]$^+$ 439.1245, found 440.1311. HPLC: t$_R$=8.43 min, 96.50%, (λ=254 nm).

Example 13 Preparation of Target Compound (Im)

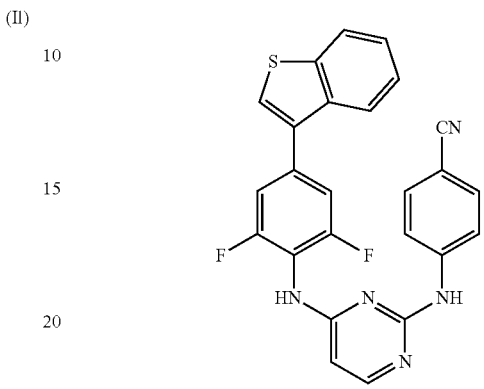

(Im)

1.0 mmol of 4-((4-((4-bromo-2,6-difluorophenyl)(methyl) amino) pyrimidin-2-yl) amino) benzonitrile, 4.0 mmol of cesium carbonate, 0.02 mmol of Pd(dppf)Cl$_2$ and 1.6 mmol of 3-benzothienyl boronic acid were added to 6 mL of 1, 4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Im) (yield: 96%; melting point: 223.3-224.0° C.).

The target compound (Im) was characterized as follows.

$^1$HNMR (400 MHz, DMSO-d$_6$) δ: 9.78 (s, 1H, NH), 9.35 (s, 1H, NH), 8.15 (d, J=4 Hz, 1H, pyrimidine-H), 8.13 (s, 1H, ArH), 8.07 (s, 1H, ArH), 8.00 (d, J=8 Hz, 1H, ArH), 7.81 (d, J=12.0 Hz, 2H, ArH), 7.58-7.47 (m, 6H, ArH), 6.38 (d, J=4.0 Hz, 1H, pyrimidine-H).

$^{13}$C NMR (100 MHz, DMSO-d$_6$) δ: 162.1, 159.6, 160.0-157.5 (dd, J$_{C-F}$=6 Hz, J$_{C-F}$=241 Hz), 157.1, 145.8, 140.6, 137.0, 135.1 (t, J$_{C-F}$=10 Hz), 134.9, 133.1, 127.0, 125.4 (d, J$_{C-F}$=12 Hz), 123.9, 122.7, 120.1, 118.5, 115.4 (t, J$_{C-F}$=16 Hz), 112.5-112.3 (dd, J$_{C-F}$=6 Hz, J$_{C-F}$=12 Hz), 102.1, 99.3.

HRMS (ESI$^+$): m/z calcd for C$_{25}$H$_{15}$F$_2$N$_5$S [M+Na]$^+$ 455.1016, found 456.1074. HPLC: t$_R$=8.85 min, 96.98%, (λ=254 nm).

Example 14 Preparation of Target Compound (In)

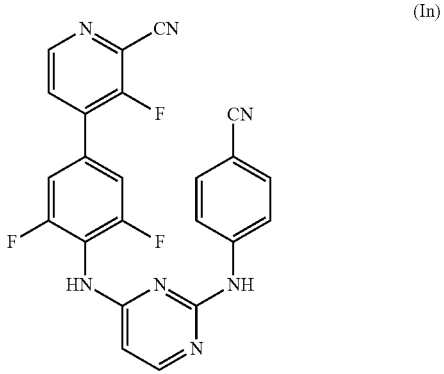 [SMILES: N#Cc1ccc(Nc2nccc(Nc3c(F)cc(-c4ccnc(C#N)c4F)cc3F)n2)cc1]
(In)

1.0 mmol of 4-((4-((4-bromo-2,6-difluorophenyl)(methyl) amino) pyrimidin-2-yl) amino) benzenonitrile, 4.0 mmol of cesium carbonate, 0.01 mmol of Pd(dppf)Cl$_2$ and 3.0 mmol of 3-fluoro-2-cyano-4-pyridyl boronic acid were added to 6 mL of 1, 4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (In) (yield: 66%; melting point: 265.4-266.1° C.).

The target compound (In) was characterized as follows.

$^1$H NMR (400 MHz, DMSO-d$_6$) δ: 9.78 (s, 1H, NH), 9.48 (s, 1H, NH), 9.19 (s, 1H, ArH), 8.66 (s, 1H, ArH), 8.16 (d, J=8 Hz, 1H, pyrimidine-H), 7.98 (d, J=8 Hz, 1H, ArH), 7.80-7.54 (dd, J=8.0 Hz, J=84 Hz, 4H, ArH), 6.39 (d, J=4.0 Hz, 1H, pyrimidine-H).

$^{13}$C NMR (100 MHz, DMSO-d$_6$) δ: 163.1, 161.6, 160.4, 159.5, 159.8-157.3 (dd, J$_{C-F}$=4 Hz, J$_{C-F}$=246 Hz), 157.3, 146.1, 146.0, 145.6, 139.5 (d, J$_{C-F}$=5 Hz), 133.2, 123.4 (d, J$_{C-F}$=19 Hz), 120.8 (d, J$_{C-F}$=15 Hz), 120.1, 118.4, 117.9 (t, J$_{C-F}$=16 Hz), 114.1 (d, J$_{C-F}$=5 Hz), 112.0-111.8 (d, J$_{C-F}$=25 Hz), 102.2, 99.5.

HRMS (ESI$^+$): m/z calcd for C$_{23}$H$_{12}$F$_3$N$_7$ [M+1]$^+$ 443.1106, found 444.1179. HPLC: t$_R$=7.62 min, 95.00%, (λ=254 nm).

Example 15 Preparation of Target Compound (Io)

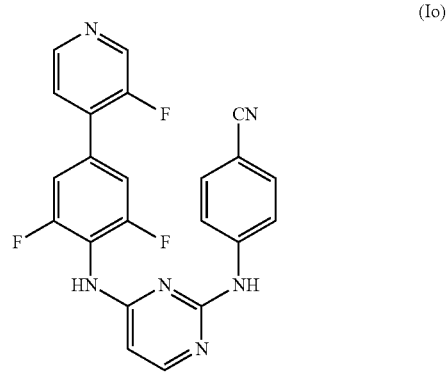 [SMILES: N#Cc1ccc(Nc2nccc(Nc3c(F)cc(-c4ccncc4F)cc3F)n2)cc1]
(Io)

1.0 mmol of 4-((4-((4-bromo-2,6-difluorophenyl)(methyl) amino) pyrimidin-2-yl) amino) benzenonitrile, 4.0 mmol of cesium carbonate, 0.01 mmol of Pd(dppf)Cl$_2$ and 5.0 mmol of 3-fluoro-4-pyridyl boronic acid were added to 6 mL of 1, 4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Io) (yield: 88%; melting point: 271.5-272.3° C.).

The target compound (Io) was characterized as follows.

$^1$H NMR (400 MHz, DMSO-d$_6$) δ: 9.78 (s, 1H, NH), 9.45 (s, 1H, NH), 8.76 (d, J=8 Hz, 1H, ArH), 8.59 (d, J=4 Hz, 1H, ArH), 8.16 (d, J=4 Hz, 1H, pyrimidine-H), 7.79-776 (m, 3H, ArH), 7.68-7.52 (dd, J=8.0 Hz, J=44 Hz, 4H, ArH), 6.39 (d, J=4.0 Hz, 1H, pyrimidine-H).

$^{13}$C NMR (100 MHz, DMSO-d$_6$) δ: 161.8, 159.5, 157.7-155.1 (d, J$_{C-F}$=255 Hz), 157.2, 157.1 (d, J$_{C-F}$=6 Hz), 146.9 (d, J$_{C-F}$=5 Hz), 145.7, 139.5 (d, J$_{C-F}$=25 Hz), 133.1, 131.6 (t, J$_{C-F}$=11 Hz), 124.8, 120.1, 118.5, 117.3 (t, J$_{C-F}$=16 Hz), 113.4 (d, J$_{C-F}$=23 Hz), 102.2, 99.4.

HRMS (ESI$^+$): m/z calcd for C$_{22}$H$_{13}$F$_3$N$_6$ [M+H]$^+$ 418.1154, found 419.1222. HPLC: t$_R$=5.83 min, 97.42%, (λ=254 nm).

Example 16 Preparation of Target Compound (Ip)

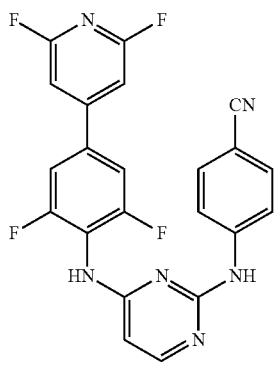

(Ip)

1.0 mmol of 4-((4-((4-bromo-2,6-difluorophenyl)(methyl) amino) pyrimidin-2-yl) amino) benzenonitrile, 4.0 mmol of cesium carbonate, 0.02 mmol of Pd(dppf)Cl$_2$ and 6.0 mmol of 2,6-difluoro-4-pyridyl boronic acid were added to 6 mL of 1,4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: hyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ip) (yield: 57%; melting point: 248.8-249.2° C.).

The target compound (Ip) was characterized as follows.

$^1$H NMR (400 MHz, DMSO-d$_6$) δ: 9.77 (s, 1H, NH), 9.48 (s, 1H, NH), 8.16 (d, J=4 Hz, 1H, pyrimidine-H), 7.99-7.53 (dd, J=8.0 Hz, J=168 Hz, 4H, ArH), 7.79-7.77 (m, 4H, ArH), 6.39 (d, J=4.0 Hz, 1H, pyrimidine-H).

$^{13}$C NMR (100 MHz, DMSO-d$_6$) δ: 163.5-161.1 (dd, $J_{C-F}$=17 Hz, $J_{C-F}$=224 Hz), 161.6, 159.5, 157.3, 155.4, 145.6, 134.1, 133.1, 120.1, 118.5, 118.3 (t, $J_{C-F}$=16 Hz), 118.3 (d, $J_{C-F}$=25 Hz), 104.7, 104.4, 102.2, 99.5.

HRMS (ESI$^+$): m/z calcd for C$_{22}$H$_{12}$F$_4$N$_6$ [M+H]$^+$ 436.1060, found 437.1132. HPLC: $t_R$=6.74 min, 98.87%, (λ=254 nm).

Example 17 Preparation of Target Compound (Iq)

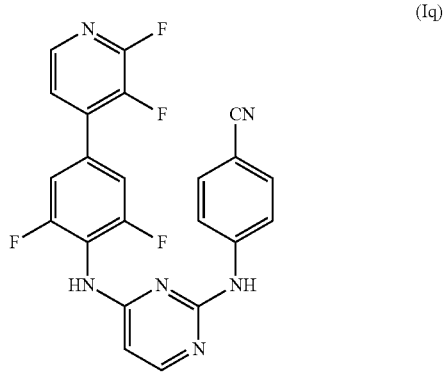 [SMILES: N#Cc1ccc(Nc2nccc(Nc3c(F)cc(-c4ccnc(F)c4F)cc3F)n2)cc1]

(Iq)

1.0 mmol of 4-((4-((4-bromo-2,6-difluorophenyl)(methyl) amino) pyrimidin-2-yl) amino) benzenonitrile, 4.0 mmol of cesium carbonate, 0.03 mmol of Pd(dppf)Cl$_2$ and 7.0 mmol of 2,3-difluoro-4-pyridyl boronic acid were added to 6 mL of 1,4-dioxane at room temperature. After the atmosphere in the reaction system was replaced with nitrogen three times, the reaction mixture was reacted under stirring at 110° C. for 10 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Iq) (yield: 65%; melting point: 257.4-257.9° C.).

The target compound (Iq) was characterized as follows.

$^1$H NMR (400 MHz, DMSO-d$_6$) δ: 9.79 (s, 1H, NH), 9.48 (s, 1H, NH), 8.16 (d, J=4 Hz, 1H, pyrimidine-H), 8.19-8.15 (m, 2H, ArH), 7.79-7.53 (dd, J=8 Hz, J=88 Hz, 4H, ArH), 7.73-7.69 (m, 3H, ArH), 6.40 (d, J=8.0 Hz, 1H, pyrimidine-H).

$^{13}$C NMR (100 MHz, DMSO-d$_6$) δ: 161.7, 159.5, 157.3, 159.5-156.9 (dd, $J_{C-F}$=16 Hz, $J_{C-F}$=241 Hz), 153.7-151.2 (dd, $J_{C-F}$=15 Hz, $J_{C-F}$=217 Hz), 145.6, 144.0-141.5 (dd, $J_{C-F}$=29 Hz, $J_{C-F}$=230 Hz), 142.2 (q, $J_{C-F}$=7 Hz), 137.5, 133.1, 130.6, 123.7, 120.1, 118.5, 117.8 (t, $J_{C-F}$=17 Hz), 113.5 (d, $J_{C-F}$=22 Hz), 102.2, 99.5.

HRMS (ESI$^+$): m/z calcd for C$_{22}$H$_{12}$F$_4$N$_6$ [M+Na]+ 436.1060, found 459.0957. HPLC: $t_R$=6.75 min, 97.58%, (λ=254 nm).

Example 18 Preparation of Target Compound (Ir)

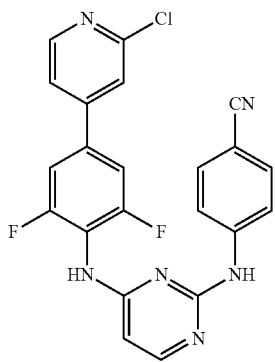

1.0 mmol of 4-((4-((4-bromo-2,6-difluorophenyl)(methyl) amino) pyrimidin-2-yl) amino) benzenonitrile, 4.0 mmol of cesium carbonate, 0.10 mmol of Pd(dppf)Cl$_2$ and 2.5 mmol of 2-fluoro-4-pyridyl boronic acid were added to 6 mL of 1,4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Ir) (yield: 80%; melting point: 196.1-197.2° C.).

The target compound (Ir) was characterized as follows.

$^1$H NMR (400 MHz, DMSO-d$_6$) δ: 10.04 (s, 1H, NH), 9.71 (s, 1H, NH), 8.82 (d, J=4 Hz, 1H, ArH), 8.44 (d, J=4 Hz, 1H, pyrimidine-H), 8.33 (s, 1H, ArH), 8.20 (d, J=8 Hz, 3H, ArH), 8.81-7.81 (dd, J=8 Hz, J=92 Hz, 4H, ArH), 6.65 (d, J=4.0 Hz, 1H, pyrimidine-H).

$^{13}$C NMR (100 MHz, DMSO-d$_6$) δ: 161.7, 159.5, 157.2, 160.0-157.4 (dd, J$_{C-F}$=6 Hz, J$_{C-F}$=241 Hz), 152.0, 151.0, 148.4, 145.7, 135.1 (t, J$_{C-F}$=10 Hz), 133.1, 121.9, 121.0, 120.1, 118.5, 117.7 (t, J$_{C-F}$=17 Hz), 111.6-111.3 (dd, J$_{C-F}$=6 Hz, J$_{C-F}$=13 Hz), 102.2, 99.4.

HRMS (ESI$^+$): m/z calcd for C$_{22}$H$_{13}$ClF$_2$N$_6$ [M+H]$^+$ 434.0858, found 457.0751. HPLC: t$_R$=6.37 min, 97.99%, (λ=254 nm).

Example 19 Preparation of Target Compound (Is)

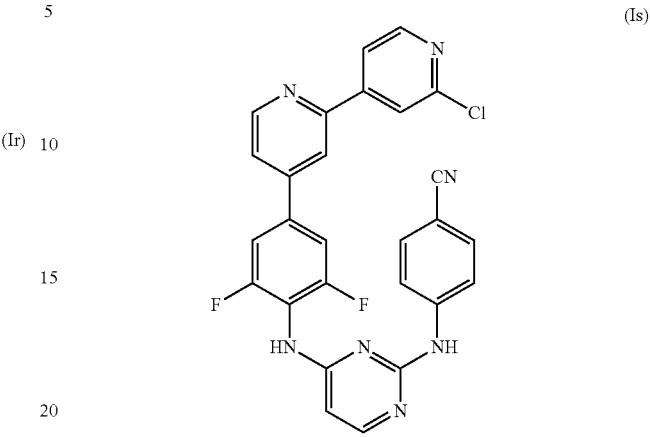

1.0 mmol of 4-((4-((4-bromo-2,6-difluorophenyl)(methyl) amino) pyrimidin-2-yl) amino) benzenonitrile, 4.0 mmol of cesium carbonate, 0.02 mmol of Pd(dppf)Cl$_2$ and 3.3 mmol of dipyridyl boronic acid were added to 6 mL of 1, 4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Is) (yield: 88%; melting point: 291.5-291.9° C.).

The target compound (Is) was characterized as follows.

$^1$H NMR (400 MHz, DMSO-d$_6$) δ: 9.77 (s, 1H, NH), 9.45 (s, 1H, NH), 8.88 (d, J=8 Hz, 1H, ArH), 8.62-8.59 (m, 2H, ArH), 8.41 (d, J=4 Hz, 1H, pyrimidine-H), 8.16 (m, 1H, ArH), 8.09-8.02 (m, 3H, ArH), 7.81-7.53 (dd, J=8 Hz, J=100 Hz, 4H, ArH), 6.39 (d, J=4.0 Hz, 1H, pyrimidine-H).

$^{13}$C NMR (100 MHz, DMSO-d$_6$) δ: 161.8, 159.5, 157.2, 160.1-157.6 (dd, J$_{C-F}$=5 Hz, J$_{C-F}$=240 Hz), 153.5, 151.9, 151.3, 151.0, 149.5, 146.4, 145.7, 136.2 (t, J$_{C-F}$=10 Hz), 133.1, 122.4, 121.8, 120.9, 120.1, 119.3, 118.5, 117.3 (t, J$_{C-F}$=17 Hz), 111.53-111.28 (dd, J$_{C-F}$=4 Hz, J$_{C-F}$=16 Hz), 102.2, 99.4.

HRMS (ESI$^+$): m/z calcd for C$_{27}$H$_{16}$ClF$_2$N$_7$ [M+H]$^+$ 511.1124, found 511.9097. HPLC: t$_R$=7.58 min, 98.27%, (λ=254 nm).

Example 20 Preparation of Target Compound (It)

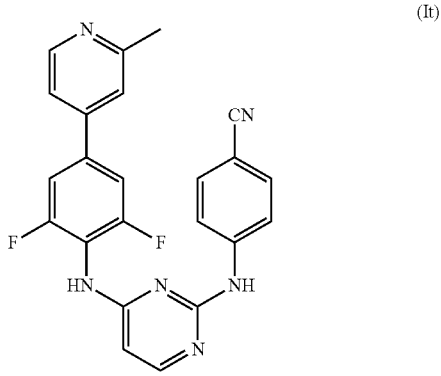

1.0 mmol of 4-((4-((4-bromo-2,6-difluorophenyl)(methyl) amino) pyrimidin-2-yl) amino) benzenonitrile, 4.0 mmol of cesium carbonate, 0.03 mmol of Pd(dppf)Cl$_2$ and 1.2 mmol of 2-methyl-4-pyridyl boronic acid were added to 6 mL of 1,4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (It) (yield: 88%; melting point: 224.4-225.1° C.).

The target compound (It) was characterized as follows.

$^1$H NMR (400 MHz, DMSO-d$_6$) δ: 9.76 (s, 1H, NH), 9.38 (s, 1H, NH), 8.56 (d, J=4 Hz, 1H, ArH), 8.14 (d, J=4 Hz, 1H, pyrimidine-H), 7.83-7.79 (m, 3H, ArH), 7.77-7.50 (dd, J=32 Hz, J=92 Hz, 4H, ArH), 7.65 (d, J=4 Hz, 1H, ArH), 6.36 (d, J=4.0 Hz, 1H, pyrimidine-H), 2.57 (s, 3H, CH$_3$).

$^{13}$C NMR (100 MHz, DMSO-d$_6$) δ: 161.9, 160.1-157.6 (dd, J$_{C-F}$=6 Hz, J$_{C-F}$=240 Hz), 159.5, 159.4, 157.2, 150.2, 145.7, 145.0, 137.1 (t, J$_{C-F}$=10 Hz), 133.1, 120.9, 120.1, 118.7, 118.5, 116.8 (t, J$_{C-F}$=16 Hz), 111.1-110.8 (dd, J$_{C-F}$=5 Hz, J$_{C-F}$=14 Hz), 102.1, 99.3, 24.6.

HRMS (ESI$^+$): m/z calcd for C$_{23}$H$_{16}$F$_2$N$_6$ [M+H]$^+$ 414.1405, found 415.1470. HPLC: t$_R$=5.83 min, 99.26%, (λ=254 nm).

Example 21 Preparation of Target Compound (Iu)

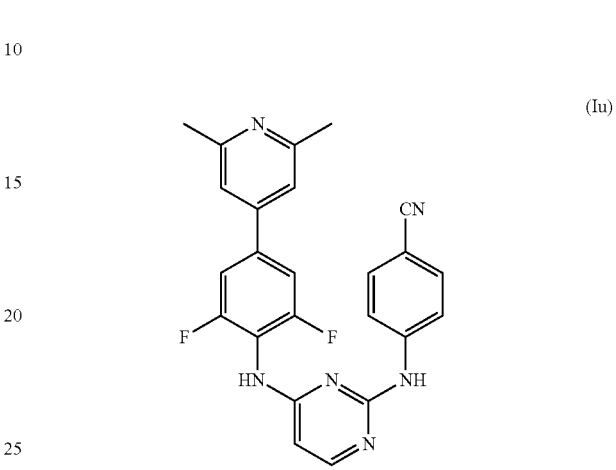

1.0 mmol of 4-((4-((4-bromo-2,6-difluorophenyl)(methyl) amino) pyrimidin-2-yl) amino) benzenonitrile, 4.0 mmol of cesium carbonate, 0.01 mmol of Pd(dppf)Cl$_2$ and 5.0 mmol of 2, 6-dimethyl-4-pyridyl boronic acid were added to 6 mL of tetrahydrofuran at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Iu) (yield: 88%; melting point: 250.1-251.0° C.).

The target compound (Iu) was characterized as follows.

$^1$H NMR (400 MHz, DMSO-d$_6$) δ: 9.77 (s, 1H, NH), 9.37 (s, 1H, NH), 8.14 (d, J=4 Hz, 1H, pyrimidine-H), 7.77 (d, J=8 Hz, 4H, ArH), 7.52-7.50 (m, 4H, ArH), 6.37 (d, J=4.0 Hz, 1H, pyrimidine-H), 2.52 (s, 6H, CH$_3$).

$^{13}$C NMR (100 MHz, DMSO-d$_6$) δ: 161.9, 160.1-157.6 (dd, J$_{C-F}$=6 Hz, J$_{C-F}$=240 Hz), 159.5, 158.6, 157.2, 145.7, 145.4, 137.5 (t, J$_{C-F}$=10 Hz), 133.1, 120.1, 118.5, 118.0, 116.7 (t, J$_{C-F}$=17 Hz), 111.0-110.8 (dd, J$_{C-F}$=5 Hz, J$_{C-F}$=13 Hz), 102.1, 99.3, 24.5.

HRMS (ESI$^+$): calcd for C$_{24}$H$_{15}$F$_2$N$_6$ [M+H]$^-$ 428.1561, found 429.1627. HPLC: t$_R$=6.51 min, 97.84%, (λ=254 nm).

Example 22 Preparation of Target Compound (Iv)

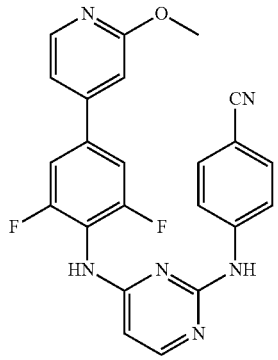

1.0 mmol of 4-((4-((4-bromo-2,6-difluorophenyl)(methyl) amino) pyrimidin-2-yl) amino) benzenonitrile, 4.0 mmol of cesium carbonate, 0.02 mmol of Pd(dppf)Cl$_2$ and 2.2 mmol of 2-methoxy-4-pyridyl boronic acid were added to 6 mL of 1, 4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Iv) (yield: 93%; melting point: 246.2-246.7° C.).

The target compound (Iv) was characterized as follows.

$^1$H NMR (400 MHz, DMSO-d$_6$) δ: 9.75 (s, 1H, NH), 9.38 (s, 1H, NH), 8.29 (d, J=8 Hz, 1H, ArH), 8.14 (d, J=4 Hz, 1H, pyrimidine-H), 7.83-7.78 (m, 4H, ArH), 7.53-7.45 (m, 3H, ArH), 7.30 (s, 1H, ArH), 6.37 (d, J=4.0 Hz, 1H, pyrimidine-H), 3.93 (s, 3H, CH$_3$).

$^{13}$C NMR (100 MHz, DMSO-d$_6$) δ: 165.1, 161.9, 159.5, 160.0-157.5 (dd, J$_{C-F}$=6 Hz, J$_{C-F}$=240 Hz), 157.2, 148.2, 147.9, 145.7, 136.7 (t, J$_{C-F}$=10 Hz), 133.1, 120.1, 118.5, 117.0 (t, J$_{C-F}$=17 Hz), 115.2, 111.2-110.9 (dd, J$_{C-F}$=5 Hz, J$_{C-F}$=13 Hz), 108.1, 99.4, 53.8.

HRMS (ESI$^+$): m/z calcd for C$_{23}$H$_{16}$F$_2$N$_6$O [M+Na]$^+$ 430.1354, found 453.1243. HPLC: t$_R$=6.89 min, 98.07%, (λ=254 nm).

Example 23 Preparation of Target Compound (Iw)

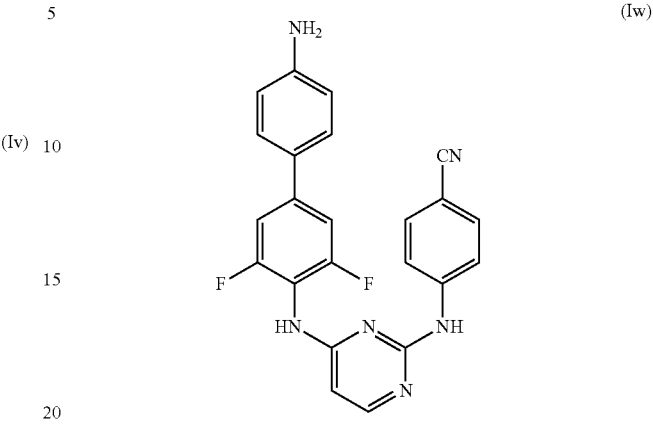

1.0 mmol of 4-((4-((4-bromo-2,6-difluorophenyl)(methyl) amino) pyrimidin-2-yl) amino) benzenonitrile, 4.0 mmol of cesium carbonate, 0.05 mmol of Pd(dppf)Cl$_2$ and 1.2 mmol of p-aminophenylboronic acid were added to 6 mL of 1,4-dioxane at room temperature. After the atmosphere in the reaction system was replaced with nitrogen three times, the reaction mixture was reacted under stirring at 110° C. for 4 h. After the raw materials were confirmed by thin layer chromatography (TLC) (eluent: ethyl acetate (EA) and petroleum ether (PE) in a volume ratio of 1:1) to be completely consumed, the reaction mixture was cooled to room temperature and sequentially washed with saturated sodium sulfite solution (20 mL×2), saturated sodium carbonate solution (20 mL×2), water (20 mL×2) and saturated saline solution (20 mL×2). The organic phases were combined, dried overnight with anhydrous sodium sulfate and filtered to collect a filtrate, which was concentrated and recrystallized with methanol to obtain a white powdery solid as the target product (Iw) (yield: 95%; melting point: 236.1-236.9° C.).

The target compound (Iw) was characterized as follows.

$^1$H NMR (400 MHz, DMSO-d$_6$) δ: 9.72 (s, 1H, NH), 9.16 (s, 1H, NH), 8.11 (d, J=4 Hz, 1H, pyrimidine-H), 7.81-7.79 (m, 2H, ArH), 7.53-7.45 (m, 6H, ArH), 6.68 (d, J=8.0 Hz, 2H, ArH), 6.30 (m, 1H, pyrimidine-H), 5.45 (s, 2H, NH$_2$).

$^{13}$C NMR (100 MHz, DMSO-d$_6$) δ: 162.3, 159.6, 157.0, 160.4-157.9 (dd, J$_{C-F}$=7 Hz, J$_{C-F}$=238 Hz), 150.0, 145.8, 141.1 (t, J$_{C-F}$=10 Hz), 133.0, 127.8, 124.8, 120.1, 118.5, 114.6, 113.0 (t, J$_{C-F}$=17 Hz), 108.7-108.5 (dd, J$_{C-F}$=6 Hz, J$_{C-F}$=13 Hz), 102.0, 99.0.

HRMS (ESI$^+$): m/z calcd for C$_{23}$H$_{16}$F$_2$N$_6$ [M+H]$^+$ 414.1405, found 415.1470. HPLC: t$_R$=5.29 min, 95.11%, (λ=254 nm).

Example 24 Salt-Formation Modification and Measurement of Water Solubility of Corresponding Salts The target products prepared in Examples 1-23 were subjected to salt formation, and the resultant salts were measured for water solubility under multiple pH conditions by a standard curve method.

The salt-formation process was described as follows. The target compound was fully dissolved in a solvent at room temperature or an elevated temperature, and then the acid corresponding to the desired salt was added, where the solvent was selected from the group consisting of methanol, ethanol, n-propanol, isopropyl alcohol, n-butanol, dichloromethane, dichloroethane, tetrahydrofuran, diethyl ether, methyl tert-butyl ether, ethyl acetate, n-hexane, cyclohexane, petroleum ether and a combination thereof.

The reaction mixture was stirred under the protection of $N_2$ for 18-48 h until a large number of solids were precipitated out, and then was filtered to collect the precipitate as the desired salt of the target compound.

The preparation of the hydrochloride of the target compound (Ia) and its water solubility test were exemplarily as follows.

100 mg of the compound (Ia) was dissolved in 15 mL of ethyl acetate at 33° C., to which 10 drops of hydrochloride acid were added. The reaction mixture was stirred at 33° C. for 24 h, and after a large number of solids was observed, the reaction mixture was filtered to obtain the target Ia•HCl complex. 5-10 mg of the Ia•acid complex was added into aqueous buffer solutions with pH of 2.0, 7.0 and 7.4, respectively, stirred at 20-25° C. for more than 18 h and filtered to obtain a supernatant. The supernatant was analyzed by reversed-phase high performance liquid chromatography (RP-HPLC) to test the water solubility of the Ia•acid complex under multiple pH conditions. The water solubility test results of several salt complexes of the compound (Ia) were shown in Table 1.

TABLE 1

Water solubility of the target compound (Ia) and several salt-formation complexes thereof

| Compound | Solubility (μg/mL) | | |
|---|---|---|---|
| | pH = 2.0 | pH = 7.0 | pH = 7.4 |
| Ia | 237 | 24.3 | 24.2 |
| Ia · HCl | 610.9 | 24.9 | 24.8 |
| Ia · HBr | 577 | 24.3 | 24.3 |
| Ia · CH$_3$SO$_2$H | 169.5 | <<1 | <<1 |
| Ia · CF$_3$SO$_2$H | 173.9 | <<1 | <<1 |
| Ia · HCO$_2$H | 557.0 | 24.6 | 24.2 |
| Ia · AcOH | 184.4 | <<1 | <<1 |
| Ia · CF$_3$COOH | 475.8 | <<1 | <<1 |
| Ia · H$_2$SO$_4$ | 35.7 | <<1 | <<1 |
| Ia · succinic acid | 146 | <<1 | <<1 |
| Ia · maleic acid | 145 | <<1 | <<1 |

Example 25 Anti-HIV Biological Activity Test

The in vitro anti-HIV biological activity of the target compounds prepared in Examples 1-23 was determined by Rega Institute of Pharmaceutical Sciences, Katholleke University, Belgium, including determination of inhibitory activity against the HIV-infected MT-4 cells and cytotoxicity. The test was performed as follows. The HIV-infected MT-4 cells were incubated in the presence of the target compound to be tested, and then the protective effect of the compound to be tested on HIV-induced cytopathy was determined by MTT assay at different time points of the HIV infection to calculate a concentration (i.e., median effective concentration $EC_{50}$) under which the target compound can protect 50% of MT-4 cells from the HIV-induced cytopathy. The toxicity test was performed in parallel with the anti-HIV activity test. The cytotoxic concentration ($CC_{50}$) under which the target compound to be tested caused 50% of uninfected MT-4 cells to experience cytopathic change was determined by the MTT assay. Moreover, a selection index ($SI=CC_5/EC_{50}$) was also calculated.

Materials and Methods

The anti-HIV activity of the compound to be tested was evaluated by the inhibitory effect on the HIV-induced cytopathy in the cell.

Cells: MT-4 cells.

Viruses: HIV-1-IIIB strain and HIV-2 ROD strain.

The compound to be tested was dissolved in DMSO or water and diluted gradiently with phosphate-buffered saline solution. 100 μL of test compound solutions of different concentrations were added to 3×10$^5$ of MT-4 cells and pre-cultured for 1 h at 37° C., respectively. 100 μL of a virus dilution at an appropriate concentration was added, and co-cultured with the MT-4 cells at 37° C. for 1 h. Then, the MT-4 cells were collected, washed three times, resuspended with a culture medium with or without the compound to be tested and cultured at 37° C. and 5% CO$_2$ for 7 d. On the third day of the infection, the culture medium was correspondingly replaced with the culture medium with or without the compound to be tested. Each culture process was repeated twice. The HIV-induced cytopathy was monitored daily with a reverse optical microscope. Generally, the cytopathic phenomenon occurred on the fifth day after the infection with the virus dilution used herein. The inhibitory concentration of a drug was expressed as the concentration ($CC_{50}$) at which the drug had a 50% inhibitory effect on the virus-induced cytopathy without direct toxicity to cells. It should be noted that when the compound to be tested was required to be dissolved in dimethylsulfoxide (DMSO) due to the poor water solubility, the concentration of the DMSO should be less than 10% with respect to water and a final concentration of the DMSO in the MT-4 cell culture media should be less than 2%. Considering that the DMSO may affect the antiviral activity of the compound to be tested, it is necessary to design a blank control using the same concentration of DMSO. In addition, the final concentration of DMSO (1/1000) should be much lower than the concentration required for HIV-1 to replicate in T cells.

This application adopted commercially-available Nevirapine (NVP), Efavirenz (EFV) and Etravirine (ETV) as positive control. Results of the anti-HIV activity and cytotoxicity of the target compounds of Examples 1-23 in the MT-4 cells were shown in Table 2, in which compounds 1-23 corresponded to the target compounds of Examples 1-23, respectively.

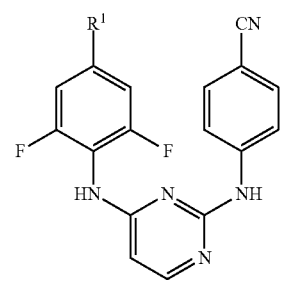

I

TABLE 2[a]

Anti-HIV activity and cytotoxicity of the target compounds of Examples 1-23 in the MT-4 cells

| compound | R[1] | EC$_{50}$(nM)[b] | CC$_{50}$(μM)[c] | SI(III$_B$)[d] |
|---|---|---|---|---|
| 1 | pyridin-4-yl | 1.0 ± 0 | >313 | >312,500 |
| 2 | pyridin-3-yl | 7.4 ± 1.76 | 242 ± 42 | 32,698 |
| 3 | pyrimidin-5-yl | 11.9 ± 3.2 | 2.7 ± 1.7 | 229 |
| 4 | furan-2-yl | 2.1 ± 0 | 16.6 ± 6.9 | 7910 |
| 5 | furan-3-yl | 3.2 ± 0.18 | 10.6 ± 1.8 | 3291 |
| 6 | thiophen-2-yl | 4.1 ± 2.0 | >308 | >74,627 |
| 7 | thiophen-3-yl | 3.9 ± 1.4 | 55.4 ± 18.7 | 14032 |
| 8 | 1H-pyrazol-4-yl | 10 ± 6.0 | 3.1 ± 1.7 | 298 |
| 9 | 2-fluoropyridin-4-yl | 3.8 ± 3.2 | 5.0 ± 0.9 | 1311 |
| 10 | 2,6-dichloropyridin-4-yl | 56 ± 32.6 | 5.4 ± 0.54 | 97 |
| 11 | 2,3-dichloropyridin-4-yl | 5.5 ± 0.7 | 20 ± 16 | 3673 |
| 12 | benzofuran-3-yl | 44 ± 10.1 | 87 ± 54 | 1991 |
| 13 | benzothiophen-3-yl | 124 ± 78 | 16 ± 6 | 132 |
| 14 | 2-cyano-3-fluoropyridin-4-yl | 1.98 ± 0.42 | >282 | >142,857 |
| 15 | 3-fluoropyridin-4-yl | 1.3 ± 0.6 | 3.3 ± 1.5 | 2566 |

TABLE 2[a]-continued

Anti-HIV activity and cytotoxicity of the target compounds of Examples 1-23 in the MT-4 cells

| compound | R[1] | EC$_{50}$(nM)[b] | CC$_{50}$(μM)[c] | SI(III$_B$)[d] |
|---|---|---|---|---|
| 16 | 2,6-difluoropyridin-4-yl | 5.6 ± 1.5 | 11 ± 6.8 | 1966 |
| 17 | 2,3-difluoropyridin-4-yl | 2.0 ± 0.48 | >286 | >147,059 |
| 18 | 2-chloropyridin-4-yl | 6.8 ± 3.4 | 4.2 ± 0.45 | 622 |
| 19 | 6'-chloro-[2,3'-bipyridin]-4-yl | 16.8 ± 3.0 | 51 ± 41 | 3068 |
| 20 | 2-methylpyridin-4-yl | 4.1 ± 1.1 | 3.2 ± 1.1 | 777 |
| 21 | 2,6-dimethylpyridin-4-yl | 56 ± 18 | 1.2 ± 0.11 | 21 |
| 22 | 2-methoxypyridin-4-yl | 13 ± 2.9 | 6.7 ± 0.98 | 501 |
| 23 | 4-aminophenyl | 9.2 ± 3.6 | >303 | >32,895 |
| NVP | — | 209 ± 66 | >15 | >72 |
| ETR | — | 4 ± 0.68 | >4.60 | >1159 |
| EFV | — | 4 ± 1.5 | >6.33 | >1600 |

[a]The data was expressed as Mean ± SD, derived from at least three independent experiments;
[b]EC$_{50}$: an effective concentration at which 50% of cells were protected from viral infection;
[c]CC$_{50}$: a concentration of a drug at which 50% of cells experienced cytopathic effect; and
[d]SI: selection index (CC$_{50}$/EC$_{50}$) for determining the safety range of a drug.

Experimental results showed that the target compounds of Examples 1-23 had strong anti-HIV-1 activity by significantly inhibiting the HIV-1 replication in the HIV-1-infected MT-4 cells. Moreover, the compounds prepared herein also had less cytotoxicity and a higher selection index.

It should be noted that though this application has been described in detail with reference to the above embodiments, it is not limited thereto. Other embodiments with same or similar technical effects as the above embodiments which are made by changing the technical parameters and raw material components within the range listed herein shall still within the protection scope of the application. Any changes, modifications and replacements made by those skilled in the art without departing from the spirit of this application should fall within the scope of this application defined by the appended claims.

What is claimed is:

1. A compound of formula (I), or a pharmaceutically-acceptable salt, a stereoisomer, a hydrate or a solvate thereof:

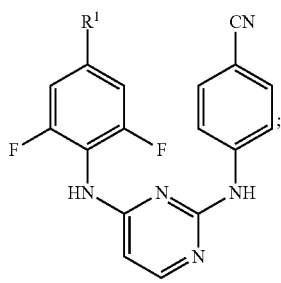

wherein R[1] is selected from the group consisting of substituted and unsubstituted furyl, substituted and unsubstituted thienyl, substituted and unsubstituted pyrazolyl, substituted and unsubstituted imidazolyl, substituted and unsubstituted thiazolyl, substituted and unsubstituted pyridyl, substituted and unsubstituted pyrimidinyl, substituted and unsubstituted p-aminophenyl and substituted and unsubstituted $C_7$-$C_{10}$ aromatic heterocyclic group.

2. The compound of claim 1, or a pharmaceutically-acceptable salt, a stereoisomer, a hydrate or a solvate thereof, wherein the compound is selected from the group consisting of:
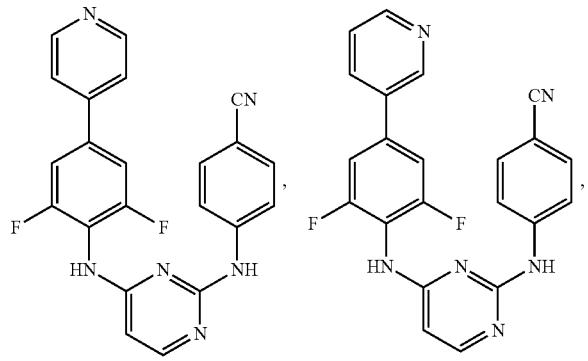
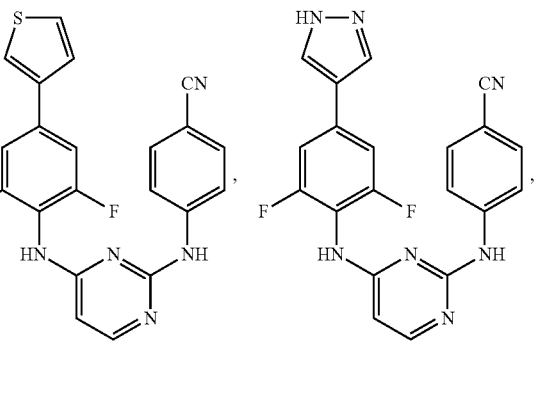
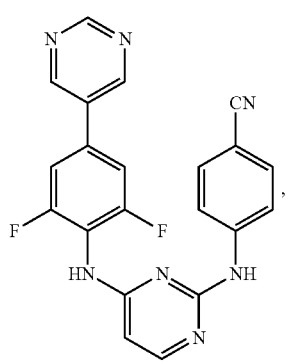
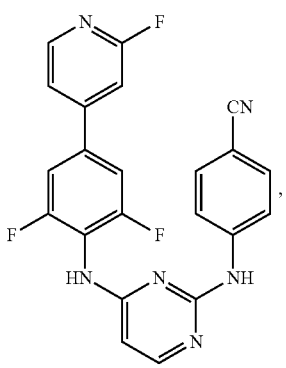
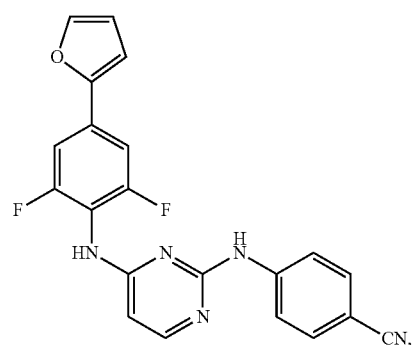
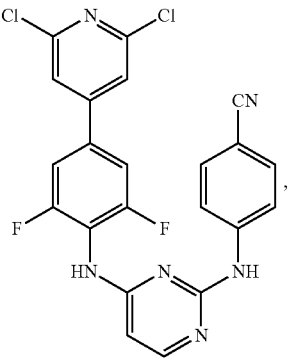
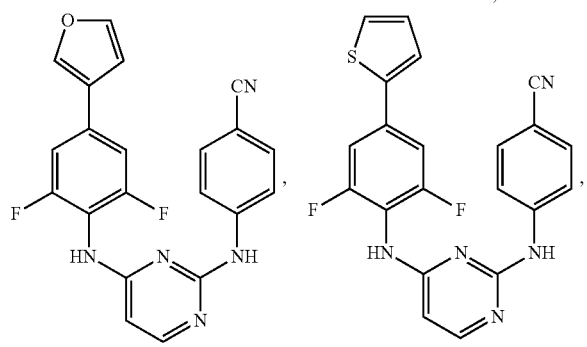

-continued

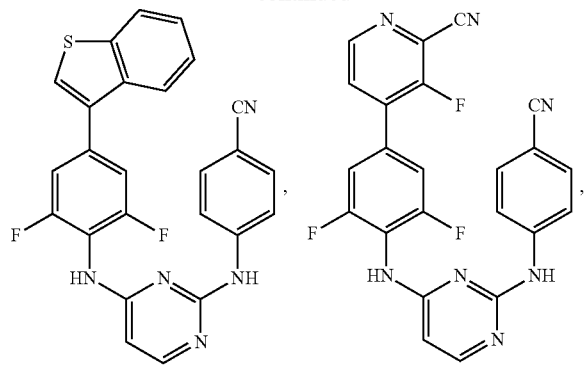

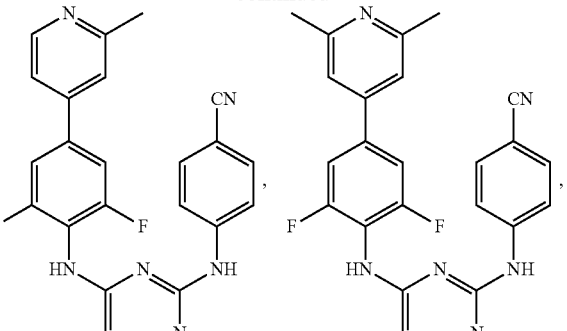

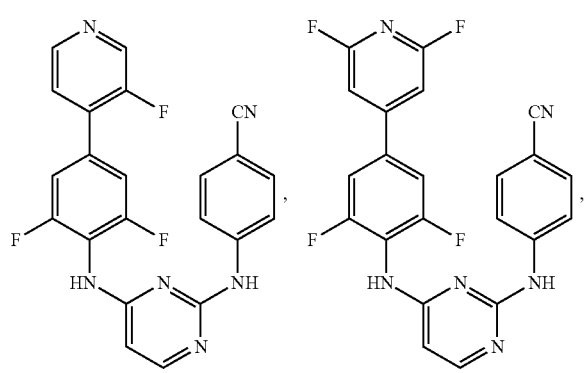

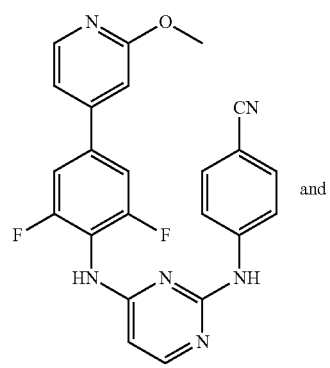

and

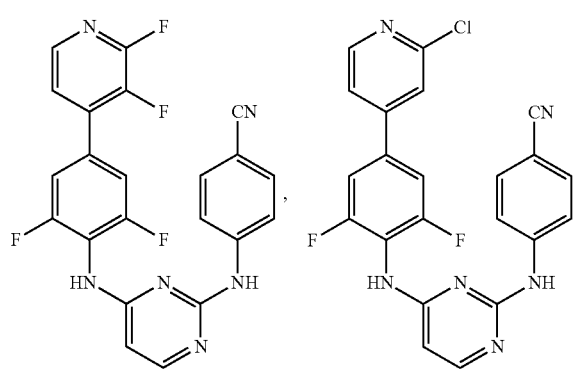

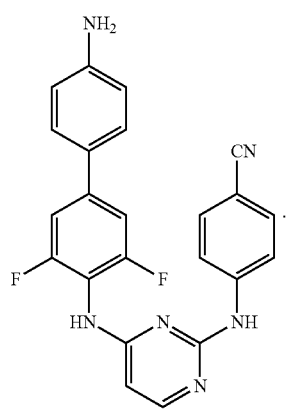

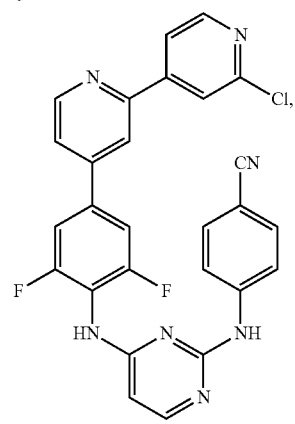

3. The compound of claim 1, or a pharmaceutically-acceptable salt, a stereoisomer, a hydrate or a solvate thereof, wherein the pharmaceutically-acceptable salt is selected from the group consisting of hydrochloride, hydrobromide, formate, methanesulfonate, trifluoromethanesulfonate, sulfate, phosphate, acetate, p-toluenesulfonate, tartrate, citrate, succinate, maleate, fumarate and malate.

4. A pharmaceutical composition, comprising a pharmaceutically effective amount of the compound of claim 1, or a pharmaceutically-acceptable salt, a stereoisomer, a hydrate or a solvate thereof, and a pharmaceutically-acceptable carrier.

5. A compound of formula (I), or a polycrystal, a eutectic or a single-enantiomer X-ray diffraction single crystal thereof:

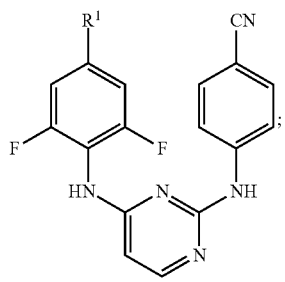

wherein R¹ is selected from the group consisting of substituted and unsubstituted furyl, substituted and unsubstituted thienyl, substituted and unsubstituted pyrazolyl, substituted and unsubstituted imidazolyl, substituted and unsubstituted thiazolyl, substituted and unsubstituted pyridyl, substituted and unsubstituted pyrimidinyl, substituted and unsubstituted p-aminophenyl and substituted and unsubstituted $C_7$-$C_{10}$ aromatic heterocyclic group.

6. The compound of claim 5, or a polycrystal, a eutectic or a single-enantiomer X-ray diffraction single crystal thereof, wherein the compound is selected from the group consisting of:

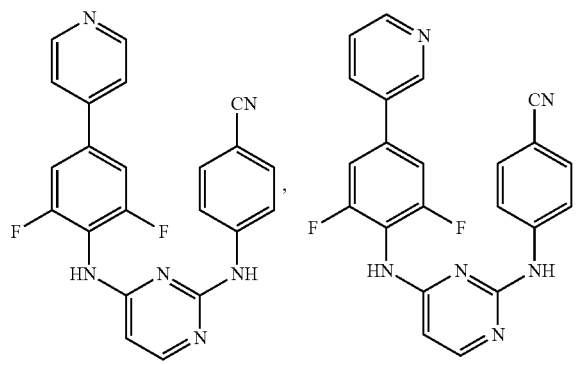

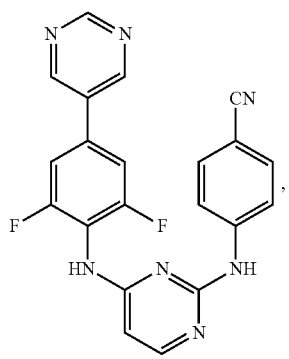

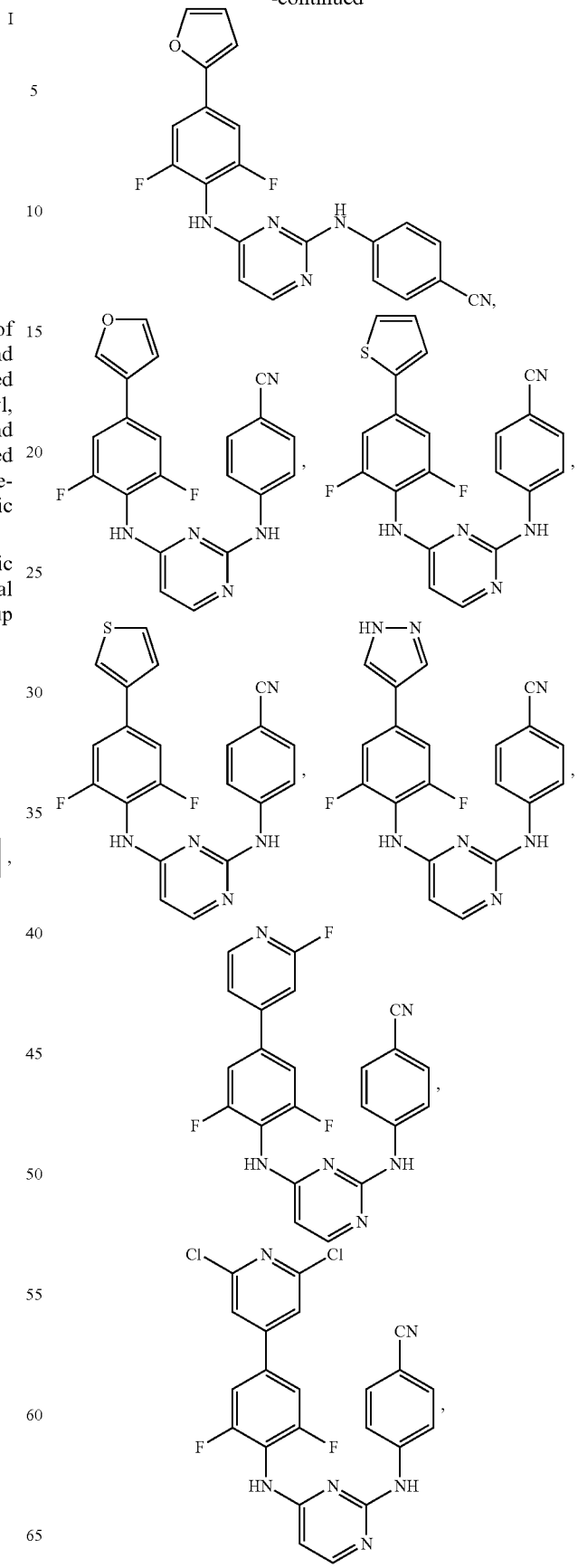

-continued
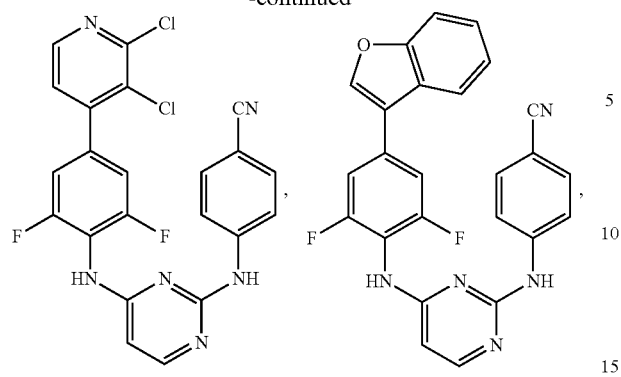
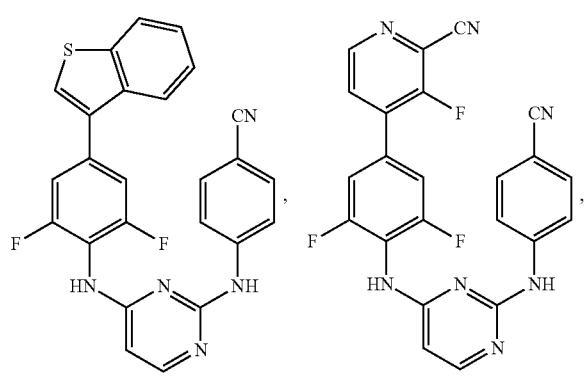
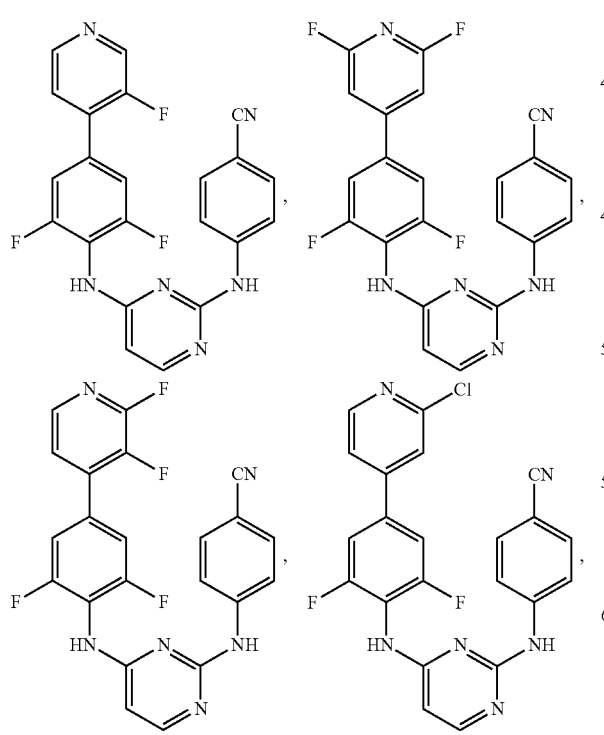
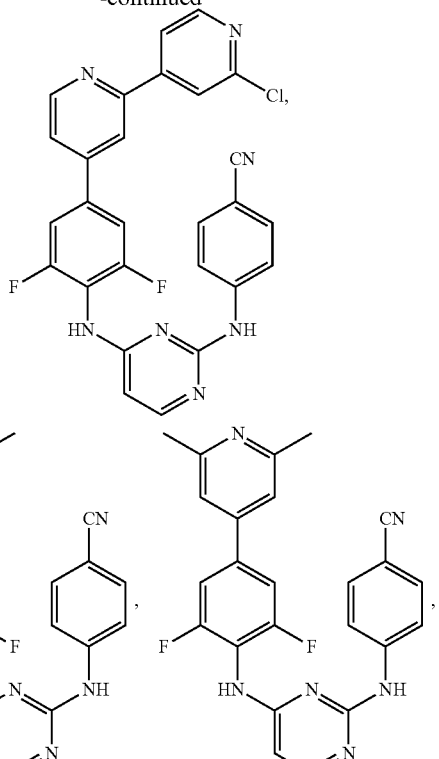
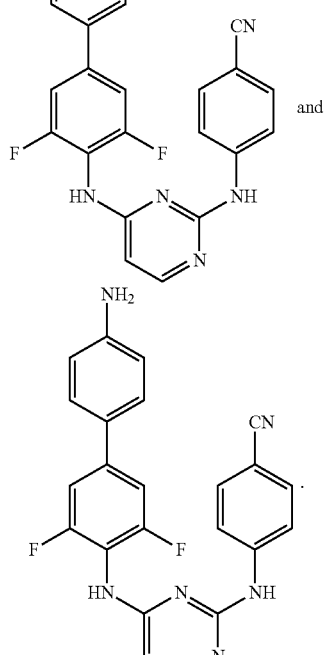
7. A pharmaceutical composition, comprising the compound of claim 5, or a polycrystal, a eutectic or a single-enantiomer X-ray diffraction single crystal thereof, and a pharmaceutically-acceptable carrier.
* * * * *